United States Patent
Collins et al.

(10) Patent No.: US 7,846,924 B2
(45) Date of Patent: *Dec. 7, 2010

(54) CYANOPYRROLES

(75) Inventors: Mark A. Collins, Norristown, PA (US); Valerie A. Mackner, Conshohocken, PA (US); Jay E. Wrobel, Lawrenceville, NJ (US); Lin Zhi, San Diego, CA (US); Todd K. Jones, Solana Beach, CA (US); Christopher M. Tegley, Thousand Oaks, CA (US); James P. Edwards, San Diego, CA (US)

(73) Assignee: Wyeth LLC, Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/184,313

(22) Filed: Jul. 19, 2005

(65) Prior Publication Data

US 2005/0256110 A1 Nov. 17, 2005

Related U.S. Application Data

(62) Division of application No. 10/342,719, filed on Jan. 15, 2003, now Pat. No. 6,982,261, which is a division of application No. 10/043,513, filed on Jan. 9, 2002, now Pat. No. 6,562,857, which is a division of application No. 09/552,544, filed on Apr. 19, 2000, now Pat. No. 6,407,101.

(60) Provisional application No. 60/183,050, filed on May 4, 1999.

(51) Int. Cl.
*A61K 31/54* (2006.01)

(52) U.S. Cl. .................................. 514/226.5

(58) Field of Classification Search ................ 514/408, 514/427, 226.5

See application file for complete search history.

(56) References Cited

U.S. PATENT DOCUMENTS

| | | | |
|---|---|---|---|
| 3,635,964 A | 1/1972 | Skorcz |
| 3,917,592 A | 11/1975 | Kobzina |
| 4,093,730 A | 6/1978 | Butti |
| 4,258,185 A | 3/1981 | Nakao et al. |
| 4,440,785 A | 4/1984 | Walsh |
| 4,666,913 A | 5/1987 | Kubla et al. |
| 4,670,566 A | 6/1987 | Walsh |
| 4,721,721 A | 1/1988 | Kuhla |
| 4,822,794 A | 4/1989 | Spada |
| 4,831,027 A | 5/1989 | Narr |
| 4,853,473 A | 8/1989 | Fischer |
| 4,933,336 A | 6/1990 | Martin et al. |
| 5,007,952 A | 4/1991 | Kume |
| 5,171,851 A | 12/1992 | Kim |
| 5,414,088 A | 5/1995 | von der Saal |
| 5,453,516 A | 9/1995 | Fischer |
| 5,475,020 A | 12/1995 | Johnson |
| 5,521,166 A | 5/1996 | Grubb |
| 5,681,817 A | 10/1997 | Hodgen |
| 5,688,808 A | 11/1997 | Jones |
| 5,688,810 A | 11/1997 | Jones |
| 5,693,646 A | 12/1997 | Jones |
| 5,693,647 A | 12/1997 | Jones |
| 5,696,127 A | 12/1997 | Jones |
| 5,696,130 A | 12/1997 | Jones |
| 5,696,133 A | 12/1997 | Jones |
| 5,719,136 A | 2/1998 | Chwalisz |

(Continued)

FOREIGN PATENT DOCUMENTS

DE 3633861 4/1988

(Continued)

OTHER PUBLICATIONS

Winneker et al. (Nonsteroidal Progesterone Receptor Modulators: Structure Activity Relationships, Seminars in Reproductive Medicine, (Feb. 2005). 23(1):46.*

(Continued)

*Primary Examiner*—Alton N Pryor
(74) *Attorney, Agent, or Firm*—Howson & Howson LLP

(57) ABSTRACT

This invention provides a progesterone receptor antagonist of formula 1 having the structure

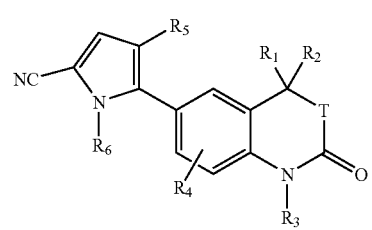

wherein, T is O, S, or absent; $R_1$, and $R_2$ are each, independently, hydrogen, alkyl, substituted alkyl; or $R_1$ and $R_2$ are taken together form a ring and together contain —$CH_2(CH_2)_n$ $CH_2$—, —$CH_2CH_2CMe_2CH_2CH_2$—, —$O(CH_2)_pCH_2$—, —$O(CH_2)_qO$—, —$CH_2CH_2OCH_2CH_2$—, or —$CH_2CH_2NR_7CH_2CH_2$—; n=1-5; p=1-4; q=1-4; $R_3$ is hydrogen, OH, $NH_2$, alkyl, substituted alkyl, alkenyl, substituted alkenyl, alkynyl, substituted alkynyl, or $COR^A$; $R^A$ is hydrogen, alkyl, substituted alkyl, alkoxy, substituted alkoxy, aminoalkyl, or substituted aminoalkyl; $R_4$ is hydrogen, halogen, CN, $NH_2$, alkyl, substituted alkyl, alkoxy, substituted alkoxy, aminoalkyl, or substituted aminoalkyl; $R_5$ is hydrogen, alkyl, or substituted alkyl; $R_6$ is hydrogen, alkyl, substituted alkyl, or $COR^B$; $R^B$ is hydrogen, alkyl, substituted alkyl, alkoxy, substituted alkoxy, aminoalkyl, or substituted aminoalkyl; $R_7$ is hydrogen or alkyl; or a pharmaceutically acceptable salt thereof.

6 Claims, No Drawings

U.S. PATENT DOCUMENTS

| | | | |
|---|---|---|---|
| 5,733,902 A | 3/1998 | Schneider | |
| 5,808,139 A | 9/1998 | Pathirana | |
| 5,874,430 A | 2/1999 | Christ | |
| 6,077,840 A | 6/2000 | Kurihara | |
| 6,306,851 B1 | 10/2001 | Santilli | |
| 6,319,912 B1 | 11/2001 | Grubb | |
| 6,329,416 B1 | 12/2001 | Grubb | |
| 6,339,098 B1 | 1/2002 | Collins | |
| 6,355,648 B1 | 3/2002 | Fensome | |
| 6,358,947 B1 | 3/2002 | Zhi et al. | |
| 6,358,948 B1 | 3/2002 | Zhang et al. | |
| 6,362,237 B1 | 3/2002 | Chwalisz et al. | |
| 6,369,056 B1 | 4/2002 | Zhang et al. | |
| 6,380,178 B1 | 4/2002 | Grubb et al. | |
| 6,380,235 B1 | 4/2002 | Zhang et al. | |
| 6,391,907 B1 | 5/2002 | Fensome et al. | |
| 6,399,593 B1 | 6/2002 | Grubb et al. | |
| 6,407,101 B1 | 6/2002 | Collins et al. | |
| 6,417,214 B1 | 7/2002 | Ullrich et al. | |
| 6,423,699 B1 | 7/2002 | Grubb et al. | |
| 6,436,929 B1 | 8/2002 | Zhang et al. | |
| 6,441,019 B2 | 8/2002 | Santilli et al. | |
| 6,444,668 B1 | 9/2002 | Grubb et al. | |
| 6,462,032 B1 | 10/2002 | Grubb et al. | |
| 6,498,154 B1 | 12/2002 | Grubb et al. | |
| 6,503,939 B2 | 1/2003 | Grubb et al. | |
| 6,509,334 B1 | 1/2003 | Zhang et al. | |
| 6,521,657 B2 | 2/2003 | Fensome et al. | |
| 6,544,970 B2 | 4/2003 | Grubb et al. | |
| 6,562,857 B2 | 5/2003 | Collins et al. | |
| 6,566,358 B2 | 5/2003 | Zhang et al. | |
| 6,566,372 B1 | 5/2003 | West et al. | |
| 6,583,145 B1 | 6/2003 | Fensome et al. | |
| 6,608,068 B2 | 8/2003 | Fensome et al. | |
| 6,693,103 B2 | 2/2004 | Zhang et al. | |
| 6,713,478 B2 | 3/2004 | Zhang et al. | |
| 6,759,408 B2 | 7/2004 | Grubb et al. | |
| 6,794,373 B2 | 9/2004 | Grubb et al. | |
| 6,835,744 B2 | 12/2004 | Zhi et al. | |
| 6,841,568 B2 | 1/2005 | Fensome et al. | |
| 6,946,454 B2 | 9/2005 | Fensome et al. | |
| 6,982,261 B2 * | 1/2006 | Collins et al. | 514/224.2 |
| 2002/0094983 A1 | 7/2002 | Zhang et al. | |
| 2002/0111355 A1 | 8/2002 | Zhang et al. | |
| 2002/0115853 A1 | 8/2002 | Zhang et al. | |
| 2002/0169198 A1 | 11/2002 | Fensome et al. | |
| 2003/0087925 A1 | 5/2003 | O'Neill et al. | |
| 2003/0092711 A1 | 5/2003 | Zhang et al. | |
| 2003/0130505 A1 | 7/2003 | Zhi et al. | |
| 2003/0158182 A1 | 8/2003 | Collins et al. | |
| 2003/0220388 A1 | 11/2003 | Fensome et al. | |
| 2004/0002535 A1 | 1/2004 | Fensome et al. | |
| 2004/0006060 A1 | 1/2004 | Fensome et al. | |
| 2004/0006122 A1 | 1/2004 | Fensome et al. | |
| 2004/0014798 A1 | 1/2004 | Fensome et al. | |
| 2004/0152719 A1 | 8/2004 | He et al. | |
| 2004/0152755 A1 | 8/2004 | He et al. | |
| 2004/0186101 A1 | 9/2004 | Zhang et al. | |
| 2005/0054711 A1 | 3/2005 | Fensome et al. | |
| 2005/0171186 A1 | 8/2005 | Fensome et al. | |
| 2006/0009509 A1 * | 1/2006 | Grubb et al. | 514/414 |
| 2006/0030615 A1 * | 2/2006 | Fensome et al. | 514/414 |
| 2006/0030717 A1 * | 2/2006 | Fensome et al. | 548/465 |

FOREIGN PATENT DOCUMENTS

| | | |
|---|---|---|
| DE | 4330234 | 3/1995 |
| DE | 4344463 | 6/1995 |
| EP | 022317 | 1/1981 |
| EP | 208510 | 1/1987 |
| EP | 311135 | 4/1989 |
| EP | 385850 | 9/1990 |
| EP | 483077 | 9/1991 |
| EP | 454330 | 10/1991 |
| EP | 535529 | 9/1992 |
| EP | 510235 | 10/1992 |
| EP | 947507 | 10/1999 |
| EP | 978279 | 2/2000 |
| JP | 63-112584 | 5/1988 |
| WO | WO-86/03749 | 7/1986 |
| WO | WO-91/06545 | 7/1986 |
| WO | WO-91/04974 | 4/1991 |
| WO | WO-91/06545 | 5/1991 |
| WO | WO-93/12085 | 6/1993 |
| WO | WO-94/14434 | 7/1994 |
| WO | WO-94/29272 | 12/1994 |
| WO | WO-9520389 * | 2/1995 |
| WO | WO-95/11013 | 4/1995 |
| WO | WO-95/20389 | 8/1995 |
| WO | WO-95/20972 | 8/1995 |
| WO | WO-95/33746 | 12/1995 |
| WO | WO-96/15794 | 5/1996 |
| WO | WO-96/19458 | 6/1996 |
| WO | WO-96/19997 | 7/1996 |
| WO | WO-97/13767 | 4/1997 |
| WO | WO-97/49407 | 12/1997 |
| WO | WO-98/10765 | 3/1998 |
| WO | WO-98/14436 | 4/1998 |
| WO | WO-98/27059 | 6/1998 |
| WO | WO-9814436 * | 6/1998 |
| WO | WO-98/55116 | 12/1998 |
| WO | WO-99/11264 | 3/1999 |
| WO | WO-99/1032503 | 3/1999 |
| WO | WO-99/15500 | 4/1999 |
| WO | WO-99/44608 | 9/1999 |
| WO | WO-01/15108 A2 | 3/2001 |
| WO | WO-01/77100 A2 | 10/2001 |
| WO | WO-2004937247 | 5/2004 |

OTHER PUBLICATIONS

Collins et al. (Novel pyrrole-containing progesterone receptor modulators, Bioorganic & Medicinal Chemistry Letters (2004), vol. 14, pp. 2185-2189.*

Winneker et al., A new generation of progesterone receptor modulators, Steroids, 2008, vol. 73, pp. 689-701.*

R. Evans, "The Steroid and Thyroid Hormone Receptor Superfamily", Science, 240:889 (May 13, 1988).

A. Ulmann et al, "Clinical Uses of Mifepristone (MFP)", Ann. N.Y. Acad. Sci., 261:248 (Jun. 12, 1995).

R. Kekkonen et al, "Sequential Regiment of the Antiprogesterone RU486 and Synthetic Progestin for Contraception", Fertility and Sterility, 60(4):610 (Oct. 1993).

K. Horwitz et al, "Progestin, Progesterone Receptors, and Breast Cancer", Horm. Cancer, publisher: Birkhaeuser, Boston, Mass., ed. Vedeckis, pp. 283-306 (1996) (abstract).

A. Murphy et al, "Regression of Uterine Leiomyomata in Response to the Antiprogesterone RU486", J. Clin. Endo. Metab., 76(2):513 (Feb. 1993).

L. Kettel et al, "Endocrine Responses to Long-Term Administration of the Antiprogesterone RU486 in Patients with Pelvic Endometriosis", Fertility and Sterility, 56(3):402 (Sep. 1991).

H. Michna et al, "Differentiation Therapy with Progesterone Antagonists", Ann. N.Y. Acad. Sci., 761:224 (Jun. 1995).

L. Zhi et al, "5-Aryl-1,2-Dihydrochromeno[3,4-f]quinolines: A Novel Class of Nonsteroidal Human Progesterone Receptor Agonists", J. Med. Chem., 41(3):291 (Oct. 22, 1998).

D. Combs et al, "Nonsteroidal Progesterone Receptor Ligands. 2. High-Affinity Ligands with Selectivity for Bone Cell Progesterone Receptors", J. Med. Chem., 38:4880 (Dec. 8, 1995).

K. Perlman et al, "20-Oxopregnacalciferols: Vitamin D Compounds that Bind the Progesterone Receptor", Tet. Letters, 35(15):2295 (1994).

L. Hamann et al, "Synthesis and Biological Activity of Novel Nonsteroidal Progesterone Receptor Antagonists", Ann. N.Y. Acad. Sci., 761:383 (Jun. 12, 1995).

R. Chen et al, "Synthesis and SAR of a Novel Series of Spirobenzothlazepine Derivatives with Antiprogestin Activity", POI-37, 16$^{th}$ Int. Cong. Het. Chem., Montana (1997).

B. Narr et al, "Preparation, Testing, and Formulation of Imidazobenzoxazinones as Cardiotonics", Chemical Abstracts, 109:22973 (1988).

R. Hartmann et al, "Effects of Brofoxine, A New Anxiolytic on Experimentally Induced Conflict in Rats", Proc. West. Pharmacol. Soc., 21:51-55 (1978).

B. Singh et al, "Novel cAMP PDE III Inhibitor" Imidazo[4,5-b]pyridin-2(3H)-ones and Thiazolo[4,5-b]pyridin-2(3H)-ones and their Analogs, J. Med. Chem., 37:248 (Jan. 21, 1994).

A. Andreani et al, "Potential Antitumor Agents XVII (1). Cytotoxic Agents from Indole Derivatives and their Intermediates", Acta. Pharm. Nord., 2(6):407 (1990).

Sakata et al, "Silver Halide Photographic Materials Useful for Platemaking", Chemical Abstracts, 123:301431 (1993).

P. Pflegel et al, "Polarografie con 7-Chlor-5-phenyl-2-thioxo-1H-2,3-dihydro-1,3,4-benzotriazepinen", Pharmazie, 37(10):714-717 (1982).

E. Barengolts et al, "Progesterone Antagonist RU486 has Bone-Sparing Effects in Ovariectomized Rats", Bone, 17(1):21 (Jul. 1995).

E. Gromachevskaya et al, "Studies of 4H-3, 1-Benzoxazines", Chem. Heterocycl. Cmpds., 33(10):1209-1214 (1997).

D. Chiarino et al, "2,1-Benzisothiazoline 2,2-Dioxide and Derivatives", J. Heterocycl. Chem., 23(6):1645-1649 (Nov.-Dec. 1986).

A. Turck et al, "On the Metabolism of 3-Substituted and 3,6-Disubstituted Pyridazines", Tetrahedron, 49(3):599-606 (1993).

V. Kumar et al, "Synthesis of 7-Azaindole and 7-Azaoxindole Derivatives through a Palladium-Catalyzed Cross-Coupling Reaction", J. Org. Chem., 57(25):6995-6998 (1992).

P. Canonne et al, "Spirocyclization of 1-(o-Aminophenyl)cycloallcanols and 1-(2'-Amino-'-pyridinyl)cycloalkanols", J Heterocyclic Chem., 26:113 (Jan.-Feb. 1989).

M-C. Forest et al, "A Novel Class of Cardiotonic Agents: Synthesis and Biological Evaluation of 5-Substituted 3,6-Dihydrothiadiazin-2-ones with Cyclic AMP Phosphodiesterase Inhibiting and Myofibrillar Calcium Sensitizing Properties", J. Med. Chem., 35:163-172 (Jan. 1992).

D. Combs et al, "Heteroatom Analogues of Bemoradan: Chemistry and Cardiotonic Activity of 1,4-Benzothiazinylpyridazinones", J. Med. Chem., 35:172-176 (Jan. 1992).

Kurihari et al., "Synthesis of (±)-PF1092A, B, and C; New Nonsteroidal Progesterone Receptor Ligands", J. Antibiotics, 50(4):360 (Apr. 1997).

A. Kende et al., "Regioselective C-3 Alkylation of Oxindole Dianion", Synth. Commun. 12(1):1 (1982).

T. Tucker et al., "Synthesis of a Series of 4-(Arilethylny1)-6-Chloro-4-Cyclopropyl-3,4-dihydroquinazolin-2(1H)-ones as Novel Non-Nucleoside HIV-1 Reverse Transcriptase Inhibitors", J. Med. Chem., 37:2347-2444 (Jul. 22, 1994).

J. Edwards et al., "5-Aryl-1,2-Dihydro-5H-Chromeno[3,4-f]Quinolines as Potent, Orally Active, Nonsteroidal Progesterone Receptor Agonists: The Effect of D-Ring Substituents", J. Med. Chem., 41:303-310 (Jan. 29, 1998).

Tatsu et al., Derwent WPI abstract of Japanese Patent No. 63-112584, "New Imidazo-Pyridine Derivatives—Useful as Platelet Agglutination Inhibitor, Antiallergic, Antiinflammatory Sedative, Cardiac, and Cardiovascular Vasodilators", (Mary 17, 1988).

Bru-Magniez et al., Derwent WPI abstract of European Patent No. 385,850, "Benzimidazole and Azabenzimidazole(s)—Having Cardiotonic, Vasodilating, Anti-Hypertensive, Anti-Aggregation, and Anti-Ulcer Activity", (Sep. 5, 1990).

Ganzer et al., Derwent WPI abstract of European Patent No. 311 135, "New Heterocycle substituted Benzo-Fused Azine and Azole Derivatives—Useful as Selective Herbicides for Pre or Post-Emergence Application", (Apr. 12, 1989).

K. Horwitz et al, "Progestin, Progesterone Receptors, and Breast Cancer", Horm. Cancer, publisher: Birkhaeuser, Boston, Mass., ed. Vedeckis, pp. 283-306 (1996).

V. Mamaev et al., "Synthesis of 4H-Thieno [3,2-B] Pyrrol-5(6H)-One" Bulletin of the Academy of Sciences on the USSR. Division of Chemical Science, US, Consultants Bureau. New York. vol. 9, p. 1549-1553, (1966).

Chwalisz et al., Derwent WPI Abstract of German Patent No. DE 4,330,234, "Female Contraceptive Method Comprises Gestation Treatment with Intermittent Progesterone Antagonist Administration.", (Mar. 9, 1995).

Stockemann, Abstract of German Patent No. 4,344,463, "Contraceptive Pack for Implantation Inhibition—Contains Competitive Progesterone Antagonist and Gestagen for Sequential Oral Administration.", (Jun. 29, 1995).

K. Kolasa et al., "Preliminary Pharmacological Studies of the Central Action of Phenyl and Piperidinomethyl Derivatives of 2-Benzoxazolone", Chemical Abstracts, vol. 99, No. 1, Abst. No. 157a (Jul. 4, 1983).

N. Meanwell et al., "Regiospecific Functionalization of 1,3-dihydro-2H-Benzimidazol-2-One and Structurally Related Cyclic Urea Derivatives", J. Organic Chem., 60(6):1565-82 (Mar. 24, 1995).

B. Singh et al., "An Efficient and Novel Synthesis of Fused Thiazol-2(3H)-ones" Heterocycles, 36(1):133-134, p. 136, compounds 16a, 18a (Jan. 1993).

G. Vernin et al., "Etude Dans la Serie des Radicaux Heterocycliques. Partie XV. Decomposition aprotique de 1' amino-6-ethyl-2-benzothiazole dans des substrats aromatiques et heteroaromatiques: preparation des mesityl-6- et furyl-6-ethyl-2-benzothiazoles, des sels quatemaires et des spiropyrannes correspondants", Helvetica Chimica Acta, 62(1/3):21-30 (Jan. 24, 1979).

Arrighi et al., "Vaginal Cytology as a Technic for Assessment of Progestational Therapy", Symposium on Effects of Progestational Agents, Acta Cytol., pp. 293-294 (May-Jun. 1962).

Abrams et al., "Selection of Patients in Early Pregnancy for Progestational Therapy", Fertility & Sterility, 15(1):84-93 (Jan.-Feb. 1964).

Lacny et al., "Cyclic Progestational Therapy of Amenorrhea", Canad. Med. Ass. J., 86:931-933 (May 19, 1962).

Pannuti et al., "Massive-Dose Progestational Therapy in Oncology (medroxyprogesterone)", Panminerva Medica, 18:129-136 (Mar.-Apr. 1976).

Zhang, "In vitro characterization of trimegestone: a new potent and selective progestin", Steroids, 65:637-643 (Oct.-Nov. 2000).

Horwitz, "Steroid receptor analysis of nine human breast cancer cell lines", Cancer Res., 38:2434-2437 (Aug. 1, 1978).

Di Lorenzo, "Progestin regulation of alkaline phosphatase in the human breast cancer cell line T47D", Cancer Res., 51:4470-4475 (Aug. 15, 1991).

Di Lorenzo, "Progesterone induced expression of alkaline phosphatase is associated with a secretory phenotype in T-47 D breast cancer cells", Biochem. Biophys, Res. Commun., 192:1066-1072 (May 14, 1993).

Hissom, "Progestin effects on growth in human breast cancer cell line T47D: possible therapeutic implications", Biochem. Biophys. Res. Commun., 145:706-711 (Jun. 15, 1987).

Musgrove, "Growth factor, steroid, and steroid antagonist regulation of cyclone gene expression associated with changes in T47D human breast cancer cell cycle progression", Mol. Cell. Biol., 13:3577-3587 (Jun. 1993).

Lamberts, "Mifepristone (U486) treatment of meningiomas", Journal of Neurology, Neurosurgery, and Psychiatry, 55(6):486-490 (Jun. 1992).

Collins, "Novel pyrrole-containing progesterone receptor modulators", Bioorganic & Medicinal Chemistry Letters, 14(9):2185-2189 (May 3, 2004).

Winneker, "Nonsteroidal progesterone receptor modulators: structure activity relationships", Seminars in Reproductive Medicine, 23(1):46 (Feb. 2005).

Winneker, "A new generation of progesterone receptor modulators", Steroids, 73(7):689-701 (Aug. 2008).

* cited by examiner

CYANOPYRROLES

CROSS-REFERENCE TO RELATED APPLICATIONS

This application is a divisional of U.S. patent application Ser. No. 10/342,719, filed Jan. 15, 2003, which is a divisional of U.S. patent application Ser. No. 10/043,513, filed Jan. 9, 2002, now U.S. Pat. No. 6,562,857, which is a divisional of U.S. patent application Ser. No. 09/552,544, filed Apr. 19, 2000, now U.S. Pat. No. 6,407,101, which claims the benefit of the priority of U.S. patent application Ser. No. 60/183,050, filed May 4, 1999, now abandoned.

BACKGROUND OF THE INVENTION

Intracellular receptors (IR) form a class of structurally related gene regulators known as "ligand dependent transcription factors" (R. M. Evans, *Science*, 240, 889, 1988). The steroid receptor family is a subset of the IR family, including progesterone receptor (PR), estrogen receptor (ER), androgen receptor (AR), glucocorticoid receptor (GR), and mineralocorticoid receptor (MR).

The natural hormone, or ligand, for the PR is the steroid progesterone, but synthetic compounds, such as medroxyprogesterone acetate or levonorgestrel, have been made which also serve as ligands. Once a ligand is present in the fluid surrounding a cell, it passes through the membrane via passive diffusion, and binds to the IR to create a receptor/ligand complex. This complex binds to specific gene promoters present in the cell's DNA. Once bound to the DNA the complex modulates the production of mRNA and protein encoded by that gene.

A compound that binds to an IR and mimics the action of the natural hormone is termed an agonist, whilst a compound that inhibits the effect of the hormone is an antagonist.

PR agonists (natural and synthetic) are known to play an important role in the health of women. PR agonists are used in birth control formulations, typically in the presence of an ER agonist, alternatively they may be used in conjunction with a PR antagonist. ER agonists are used to treat the symptoms of menopause, but have been associated with a proliferative effect on the uterus that can lead to an increased risk of uterine cancers. Co-administration of a PR agonist reduces or ablates that risk.

Jones et al (U.S. Pat. No. 5,688,810) described the PR antagonist dihydroquinoline A.

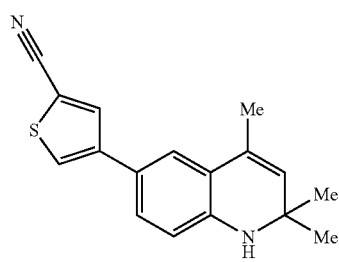

A

Jones et al described the enol ether B (U.S. Pat. No. 5,693,646) as a PR ligand.

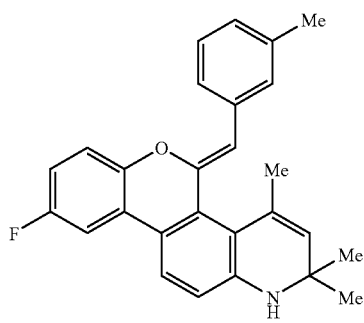

B

Jones et al described compound C (U.S. Pat. No. 5,696,127) as a PR ligand.

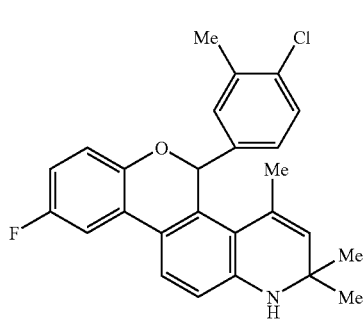

C

Zhi et al described lactones D, E and F as PR antagonists (*J. Med. Chem.* 41, 291, 1998).

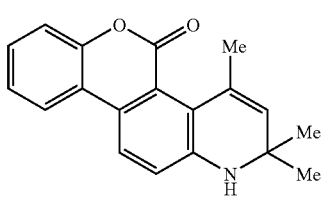

D

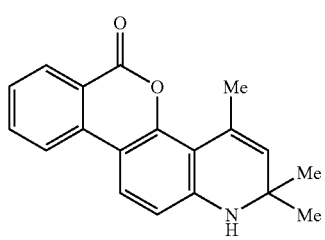

E

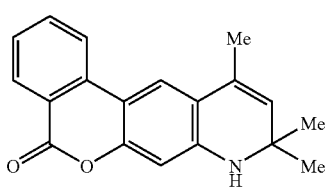

F

Zhi et al described the ether G as a PR antagonist (*J. Med. Chem.* 41, 291, 1998).

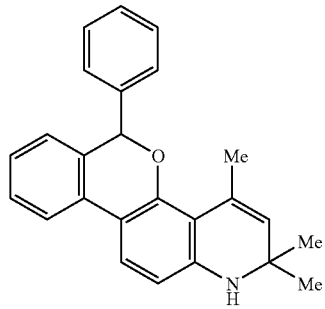

Combs et al disclosed the amide H as a ligand for the PR (*J. Med. Chem.* 38, 4880, 1995).

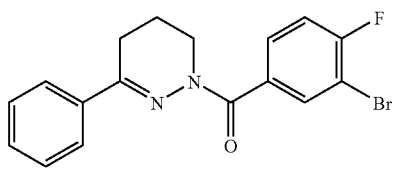

Perlman et al described the vitamin D analog I as a PR ligand (*Tetrahedron. Lett.* 35, 2295, 1994).

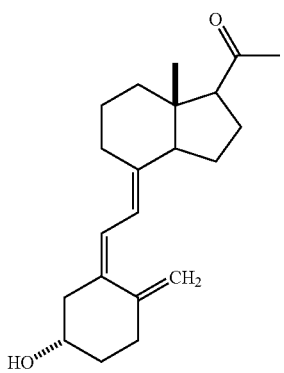

Hamann et al described the PR antagonist J (*Ann. N.Y. Acad. Sci.* 761, 383, 1995).

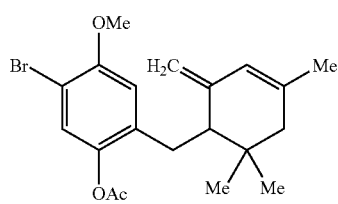

Chen et al described the PR antagonist K (Chen et al, POI-37, 16th Int. Cong. Het. Chem., Montana, 1997).

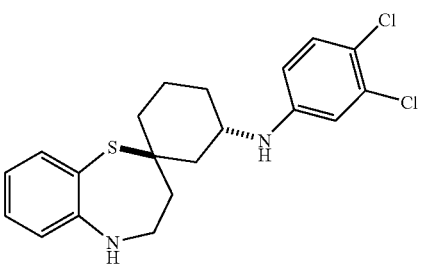

Kurihari et al described the PR ligand L (*J. Antibiotics* 50, 360, 1997).

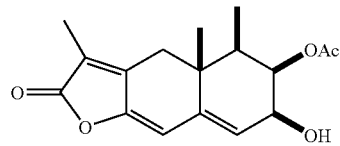

Kuhla et al claimed the oxindole M as a cardiotonic (WO 86/03749).

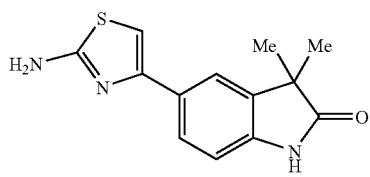

Weber claimed the oxindole N for cardiovascular indications (WO 91/06545).

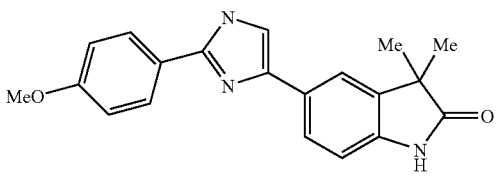

Fischer et al claim a preparation for making compounds which include the generic structure O (U.S. Pat. No. 5,453,516).

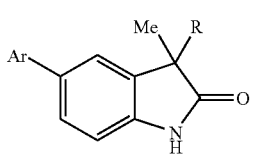

R = various

Singh et al described the PDE III inhibitor P (*J. Med. Chem.* 37, 248, 1994).

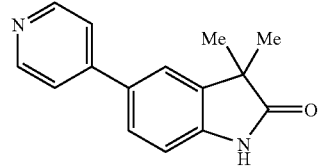

P

Andreani et al described the cytotoxic agent Q (*Acta. Pharn. Nord.* 2, 407, 1990).

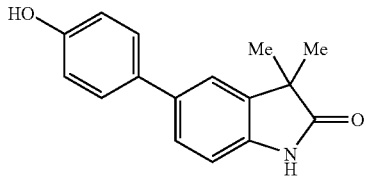

Q

Binder et al described structure R which is an intermediate for preparing COX II inhibitors (WO 97/13767).

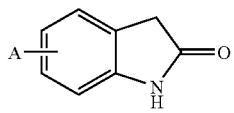

R

Walsh (A. H. Robins) described the oxindole S as an intermediate (U.S. Pat. No. 4,440,785, U.S. Pat. No. 4,670,566).

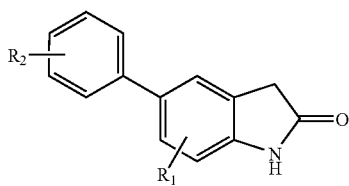

S $R_1$ = F, Cl, Br, alkyl, $NH_2$
$R_2$ = alkyl, alkoxy, F, Cl, $NH_2$, $CF_3$

Bohm et al claim the oxindole T as cardiovascular agents (WO 91/06545).

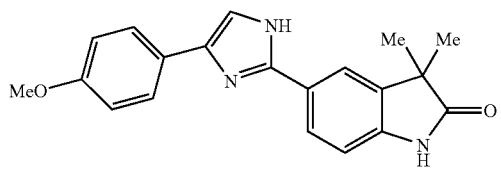

T

Bohm et al include the generic structure U (WO 91/04974).

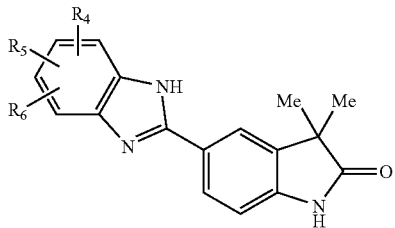

U

A Japanese patent contains the generic structure V (JP 63112584 A).

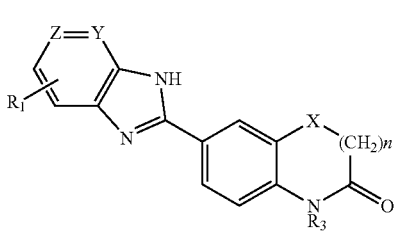

V

Boar et al described the dioxolane W as an intermediate for preparation of acetyl-cholinesterase inhibitors (WO 93/12085 A1).

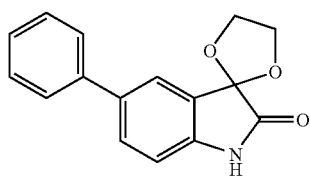

W

Kende et al described methodology for preparing 3,3-substituted oxindoles, e.g., X, that was utilized in the present invention (*Synth. Commun.* 12, 1, 1982).

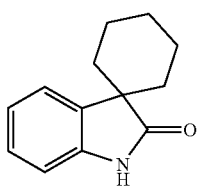

X

There are numerous literature reports that disclose a number of benzoxazin-2-ones. However, none of these examples in these patents contain substituents necessary for the compounds to be active as progesterone receptor modulators.

Among these publications, Narr et al (German Patent No. DE 3633861, CA 109:22973) discussed imidazobenzoxazinones, e.g. Y, as cardotonics. Benzoxazin-2-ones, such as brofoxine (Z), being active as an anxiolytic was reported by Hartmann et al (*Proc. West. Pharmacol. Soc.* 21, 51-55 (1978)). More recently, a number of patents (e.g., Young et al WO95/20389; Christ et al. WO98/14436) claimed quinazolin-2-ones and benzoxazin-2-ones such as compounds AA and BB as inhibitors of HIV reverse transcriptase.

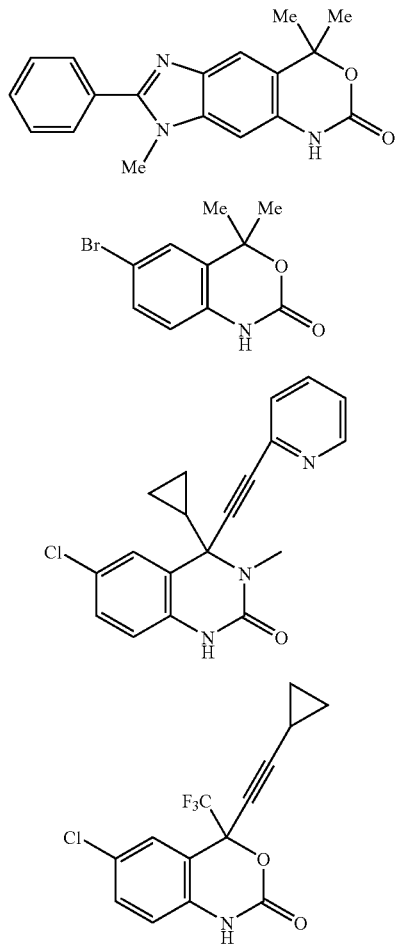

DESCRIPTION OF THE INVENTION

This invention provides progesterone receptor agonists of Formula 1 having the structure:

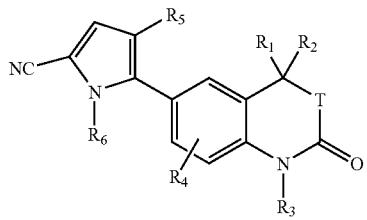

wherein, T is O, S, or absent; $R_1$, and $R_2$ are each, independently, hydrogen, alkyl, substituted alkyl; or $R_1$ and $R_2$ are taken together form a ring and together contain —$CH_2(CH_2)_n$ $CH_2$—, —$CH_2CH_2CMe_2CH_2CH_2$—, —$O(CH_2)_pCH_2$—, —$O(CH_2)_qO$—, —$CH_2CH_2OCH_2CH_2$—, or —$CH_2CH_2NR_7CH_2CH_2$—; n=1-5; p=1-4; q=1-4; $R_3$ is hydrogen, OH, $NH_2$, alkyl, substituted alkyl, alkenyl, substituted alkenyl, alkynyl, substituted alkynyl, or $COR^A$; $R^A$ is hydrogen, alkyl, substituted alkyl, alkoxy, substituted alkoxy, aminoalkyl, or substituted aminoalkyl; $R_4$ is hydrogen, halogen, CN, $NH_2$, alkyl, substituted alkyl, alkoxy, substituted alkoxy, aminoalkyl, or substituted aminoalkyl; $R_5$ is hydrogen, alkyl, or substituted alkyl;

$R_6$ is hydrogen, alkyl, substituted alkyl, or $COR^B$; $R^B$ is hydrogen, alkyl, substituted alkyl, alkoxy, substituted alkoxy, aminoalkyl, or substituted aminoalkyl;

$R_7$ is hydrogen or alkyl;

Methods of providing progestational therapy to a mammal in need thereof are provided which include administering a progestationally effective amount of compound formula 1 having the structure:

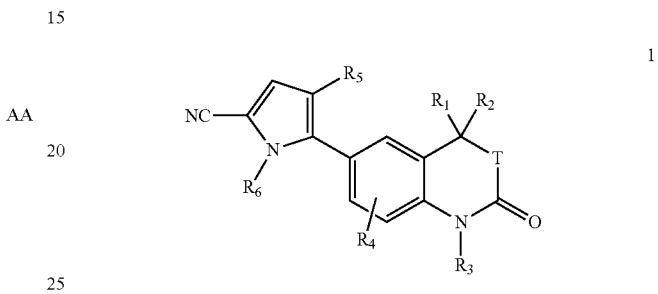

wherein, T is O, S, or absent; $R_1$, and $R_2$ are each, independently, hydrogen, alkyl, substituted alkyl; or $R_1$ and $R_2$ are taken together form a ring and together contain —$CH_2(CH_2)_n$ $CH_2$—, —$CH_2CH_2CMe_2CH_2CH_2$—, —$O(CH_2)_pCH_2$—, —$O(CH_2)_qO$—, —$CH_2CH_2OCH_2CH_2$—, or —$CH_2CH_2NR_7CH_2CH_2$—; n=1-5; p=1-4; q=1-4; $R_3$ is hydrogen, OH, $NH_2$, alkyl, substituted alkyl, alkenyl, substituted alkenyl, alkynyl, substituted alkynyl, or $COR^A$; $R^A$ is hydrogen, alkyl, substituted alkyl, alkoxy, substituted alkoxy, aminoalkyl, or substituted aminoalkyl; $R_4$ is hydrogen, halogen, CN, $NH_2$, alkyl, substituted alkyl, alkoxy, substituted alkoxy, aminoalkyl, or substituted aminoalkyl; $R_5$ is hydrogen, alkyl, or substituted alkyl; $R_6$ is hydrogen, alkyl, substituted alkyl, or $COR^B$; $R^B$ is hydrogen, alkyl, substituted alkyl, alkoxy, substituted alkoxy, aminoalkyl, or substituted aminoalkyl; $R_7$ is hydrogen or alkyl; or a pharmaceutically acceptable salt thereof, to a mammal.

or a pharmaceutically acceptable salt thereof, which are useful for contraception, in the treatment of fibroids, endometriosis, breast, uterine, ovarian and prostate cancer, and post menopausal hormone replacement therapy.

Desired compounds of this invention are those having the structure:

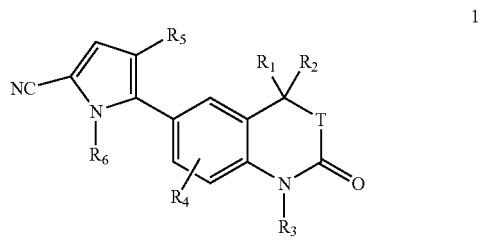

wherein, T is O, or absent; $R_1$, and $R_2$ are each, independently, hydrogen, alkyl, substituted alkyl; or $R_1$ and $R_2$ are taken together form a ring and together contain —$CH_2(CH_2)_n$ $CH_2$—; n=1-5; $R_3$ is hydrogen; R4 is hydrogen or halogen; $R_5$ is hydrogen or alkyl; $R_6$ is hydrogen or alkyl; or a pharmaceutically acceptable salt thereof.

The compounds of this invention may contain an asymmetric carbon atom and some of the compounds of this invention may contain one or more asymmetric centers and may thus give rise to optical isomers and diastereoisomers. While shown without respect to stereochemistry in Formula 1, the present invention includes such optical isomers and diastereoisomers; as well as the racemic and resolved, enantiomerically pure R and S stereoisomers; as well as other mixtures of the R and S stereoisomers and pharmaceutically acceptable salts thereof.

The compounds of this invention have been shown to act as competitive inhibitors of progesterone binding to the PR and act as agonists in functional models, either/or in-vitro and in-vivo. These compounds may be used for contraception, in the treatment of fibroids, endometriosis, breast, uterine, ovarian and prostate cancer, and post menopausal hormone replacement therapy.

The term "alkyl" is used herein to refer to both straight- and branched-chain saturated aliphatic hydrocarbon groups having 1-6 carbon atoms; "alkenyl" includes both straight- and branched-chain alkyl groups of 2-6 carbon atoms containing at least one carbon-carbon double bond; "alkynyl" group includes both straight- and branched-chain alkyl groups of 2-6 carbon atoms with at least one carbon-carbon triple bond.

The terms "substituted alkyl", "substituted alkenyl", and "substituted alkynyl" refer to alkyl, alkenyl, and alkynyl as containing one or more substituents from the group including halogen, CN, OH, $NO_2$, amino, aryl, heterocyclic, substituted aryl, substituted heterocyclic, alkoxy, aryloxy, substituted alkyloxy, alkylcarbonyl, alkylcarboxy, alkylamino, arylthio. These substituents may be attached to any carbon of alkyl, alkenyl, or alkynyl group provided that the attachment constitutes a stable chemical moiety.

The term "thioalkyl" is used herein to refer to the SR group, where R is alkyl or substituted alkyl.

The term "alkoxy" is used herein to refer to the OR group, where R is alkyl or substituted alkyl.

The term "aryloxy" is used herein to refer to the OR group, where R is aryl or substituted aryl.

The term "alkylcarbonyl" is used herein to refer to the RCO group, where R is alkyl or substituted alkyl.

The term "alkylcarboxy" is used herein to refer to the COOR group, where R is alkyl or substituted alkyl. This term is also referred to as alkoxycarbonyl.

The term "aminoalkyl" refers to both secondary and tertiary amines wherein the alkyl or substituted alkyl groups may be either same or different and the point of attachment is on the nitrogen atom.

The term "halogen" is defined as Cl, Br, F, and I.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids. Salts may also be formed from inorganic bases, preferably alkali metal salts, for example, sodium, lithium, or potassium, and organic bases, such as ammonium, mono-, di-, and trimethylammonium, mono-, di- and triethylammonium, mono-, di- and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl piperidinium, 2-methylpiperidinium, 1-ethyl-2-methylpiperidinium, mono-, di- and triethanolammonium, ethyl diethanolammonium, n-butylmonoethanolammonium, tris(hydroxymethyl)methylammonium, phenylmonoethanolammonium, and the like.

The compounds of this invention were be prepared according to the following schemes from commercially available starting materials or starting materials which can be prepared using literature procedures. These schemes show the preparation of representative compounds of this invention.

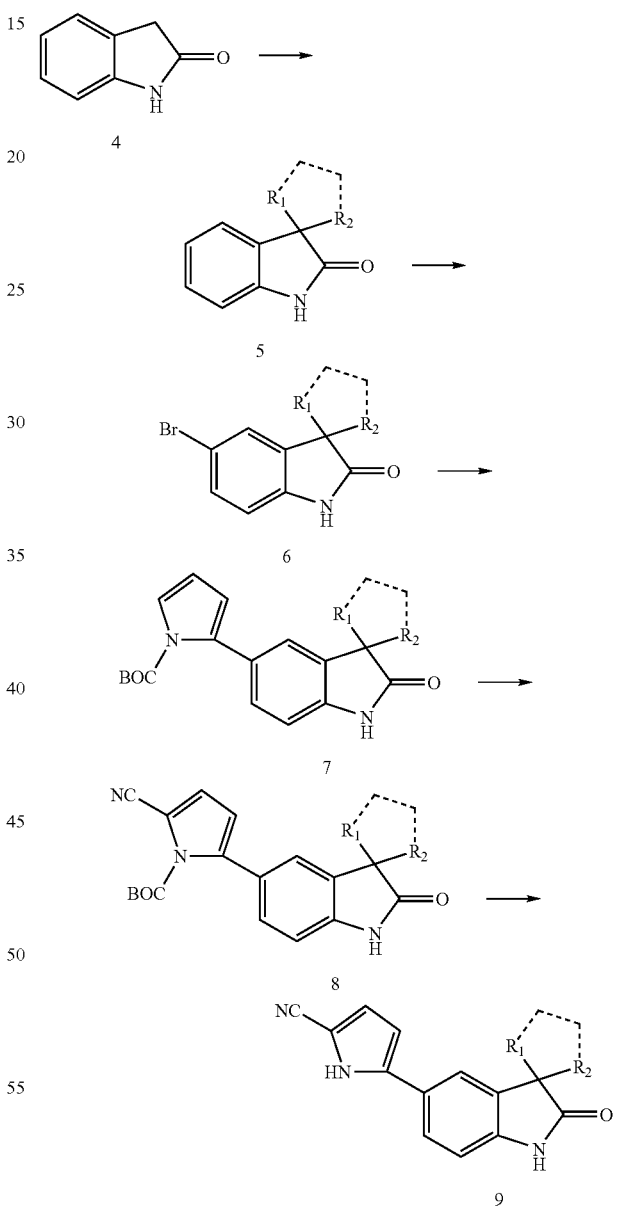

According to scheme 1, commercially available oxindole 4 is treated with a strong organo-metallic base (e.g., butyl lithium, lithium diisopropylamide, potassium hexamethyldisilazide) in an inert solvent (e.g. THF, diethyl ether) under nitrogen at reduced temperature (ca. −20° C.) (Kende, et al, Synth. Commun. 12, 1, 1982). The resulting di-anion then is treated with excess electrophile such as an alkyl halide, preferably an iodide. If $R_1$ and $R_2$ are to be joined such as the product 5 contains a spirocycle at position 3, then the electrophile should be bifunctional, i.e. a diiodide. Subsequent bromination of 5 proceeds smoothly with bromine in acetic acid (an organic co-solvent such as dichloromethane may be added as required) in the presence of sodium acetate, to afford the aryl bromide 6. The bromide 6 is reacted with a palladium salt (e.g., tetrakis(triphenylphosphine)palladium(0) or palladium acetate), in a suitable solvent (e.g., THF, dimethoxyethane, acetone, ethanol or toluene) at room temperature under an inert atmosphere (argon, nitrogen). The mixture is then treated with pyrrole 2-boronic acid (*Synthesis* 613, 1991) and a base (potassium carbonate, triethylamine, potassium phosphate) in water or fluoride source (cesium fluoride) under anhydrous conditions. Treatment of the biaryl compound 7 with chlorosulfonyl isocyanate followed by an excess of DMF at low temperature produces the protected cyanopyrrole 8. Removal of the tert-butyloxycarbonyl (BOC) protecting group via standard conditions (e.g., TFA/dichloromethane, aqueous NaOH, thermolysis) produces the required final product which is purified by standard means.

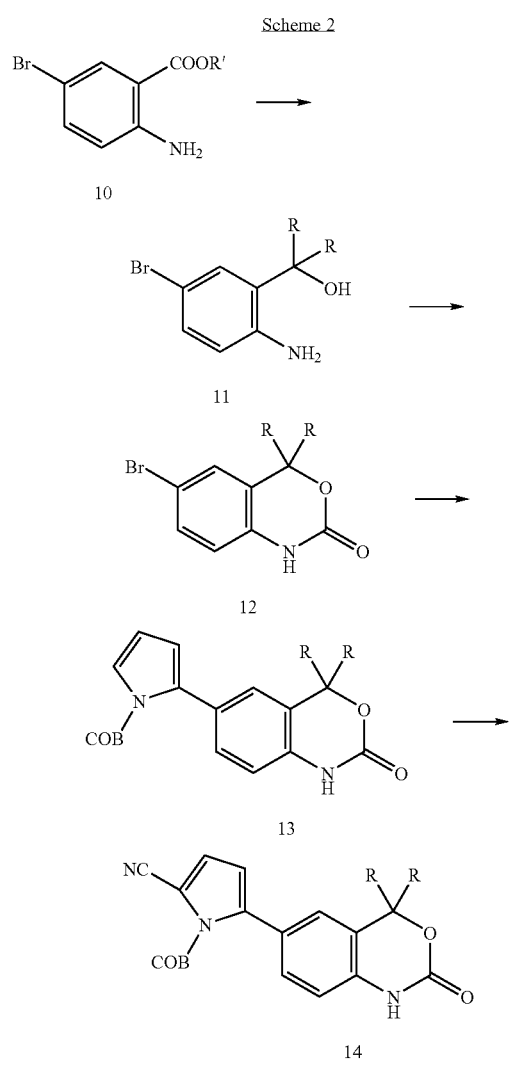

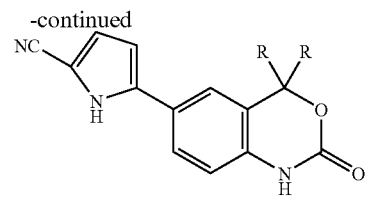

As depicted in Scheme 2, an appropriately substituted ortho-amino benzoic acid, or derivative (such as ethyl ester) 10 is treated with a suitable organometallic reagent, e.g., Grignard reagent, in appropriate nonprotic solvents (e.g., THF, ether, toluene) under an inert atmosphere such as argon or nitrogen at −78° C. to room temperature to give ortho-amino carbinol 11. Ring closure of carbinol 11 to yield benzoxazin-2-ones 12 is commonly effected by a condensing agent (e.g., carbonyldiimidazole, phosgene, dimethylcarbonate, diethylcarbonate) in a suitable nonprotic solvent (e.g., THF, ether, toluene) at temperatures in the range of room temperature to 65° C. The pyrrole ring is attached to this platform by employing a suitable coupling reaction (e.g., Suzuki, Stille) to give the biaryl 13. These reactions are performed in the presence of suitable catalyst (e.g., palladium or nickel complexes often with phosphino ligands, e.g., $Ph_3P$, dppf, dppe or palladium salts such as palladium acetate) and a base: the commonly used bases include (but are not limited to) sodium bicarbonate, sodium carbonate, potassium phosphate, barium carbonate, potassium acetate, or cesium fluoride. The most commonly used solvents in these reactions include benzene, DMF, isopropanol, ethanol, DME, ether, acetone or a mixture of any one of these solvent and water. The coupling reaction generally is executed under an inert atmosphere such as nitrogen or argon at temperatures ranging from room temperature to 95° C. Treatment of the biaryl compound 13 with chlorosulfonyl isocyanate followed by an excess of DMF at low temperature produces the protected cyanopyrrole 14. Removal of the tert-butyloxycarbonyl (BOC) protecting group via standard conditions (e.g., TFA/dichloromethane, aqueous NaOH, thermolysis) produces the required final product 15 which is purified by standard means.

The compounds of this invention are progestational agonists, and are therefore useful as oral contraceptives (male and female), in hormone replacement therapy (particularly when combined with an estrogen), in the treatment of endometriosis, luteal phase defects, benign breast and prostatic diseases and prostatic, breast, ovarian, uterine and endometrial cancers.

The compounds of this invention can be used alone as a sole therapeutic agent or can be used in combination with other agents, such as other estrogens, progestins, or androgens.

The compounds of this invention can be formulated neat or with a pharmaceutical carrier for administration, the proportion of which is determined by the solubility and chemical nature of the compound, chosen route of administration and standard pharmacological practice. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compounds of this invention can also be administered orally either in liquid or solid composition form.

The compounds of this invention may be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage requirements vary with the particular compositions employed, the route of administration, the severity of the symptoms presented and the particular subject being treated. Based on the results obtained in the standard pharmacological test procedures, projected daily dosages of active compound would be 0.02 µg/kg-750 µg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packaged powders, vials, ampoules, pre filled syringes or sachets containing liquids. The unit dosage form can be, for example, a capsule or tablet itself, or it can be the appropriate number of any such compositions in package form.

The following provides the preparation of representative compounds of this invention.

EXAMPLE 1

5-(4,4-Dimethyl-2-oxo-1,4-dihydro-2H-benzo[d][1,3]oxazin-6-yl)-1H-pyrrole-2-carbonitrile A solution of 2-amino-5-bromobenzoic acid (10 g, 46 mmol) in dry THF (200 mL) was treated at −78° C. under nitrogen with a solution of methylmagnesium bromide in ether (3.0 M, 90 mL, 270 mmol). The reaction mixture was slowly warmed to ambient temperature, kept stirring for 48 hours under nitrogen and then poured into a cold 0.5 N aqueous hydrochloride solution (300 mL). The mixture was neutralized with aqueous 1 N sodium hydroxide solution and ethyl acetate (300 mL) was added. The organic layer was separated and aqueous layer was extracted with ethyl acetate (3×100 mL). The combined organic layers were washed with brine and dried (MgSO$_4$). After removal of solvent in vacuo, the residue was purified by a silica gel flash chromatography (hexane:ethyl acetate/3:2) to give 2-(2-amino-5-bromophenyl)propan-2-ol as an off-white solid (6 g, 57%): mp 62-63° C.; $^1$H-NMR (CDCl$_3$) δ 7.19 (d, 1H, J=2.3 Hz), 7.12 (dd, 1H, J=8.4, 2.3 Hz), 6.51 (d, 1H, J=8.4 Hz), 4.70 (s, 2H), 1.82 (s, 1H), 1.65 (s, 6H).

To a solution of 2-(2-amino-5-bromophenyl)propan-2-ol (18 g, 78 mmol) in dry THF (150 mL) was added 1,1'-carbonyldiimidazole (15.5 g, 94 mmol) under nitrogen. The reaction solution was heated at 50° C. overnight. The solvent was removed in vacuo and the residue was dissolved in ethyl acetate (100 mL). The solution was washed with 1N aqueous hydrochloride solution (2×40 mL), brine (20 mL), and dried with MgSO$_4$. After removal of the solvent in vacuo, 6-bromo-4,4-dimethyl-1,4-dihydro-benzo[d][1,3]oxazin-2-one was obtained as a white solid (20 g, 100%): mp 199-200° C.; $^1$H-NMR (DMSO-d$_6$) δ 10.32 (s, 1H, D$_2$O exchangeable), 7.48 (d, 1H, J=2.1 Hz), 7.43 (dd, 1H, J=8.5, 2.1 Hz), 6.84 (d, 1H, J=8.4 Hz), 1.61 (s, 6H).

A solution of 6-bromo-4,4-dimethyl-1,4-dihydro-benzo [d][1,3]oxazin-2-one (5.0 g, 20 mmol) and tetrakis(triphenylphosphine)palladium(0) (580 mg, 0.5 mmol) in toluene (200 mL) was stirred under a flow of nitrogen for 25 min. To the solution was added sequentially 1-tert-butoxycarbonylpyrrole-2-boronic acid (8.24 g, 39 mmol) in absolute ethanol (50 mL) and potassium carbonate (5.39 g, 39 mmol) in water (50 mL). The mixture was heated to 80° C. for 16 hours and allowed to cool. The reaction mixture was poured into aqueous saturated sodium bicarbonate solution (200 mL) and extracted with ethyl acetate (3×200 mL). The organic layers were combined, washed with water (200 mL) and brine (100 mL) and dried over magnesium sulfate. The solution was filtered, concentrated in vacuo, and the residue was purified by flash column chromatography on silica gel (30% ethyl acetate/hexane) to give 2-(4,4-dimethyl-2-oxo-1,4-dihydro-2H-benzo[d][1,3]oxazin-6-yl)-pyrrole-1carboxylic acid tert-butyl ester (4.0 g, 58%) as a tan solid, mp 172-173° C.

To a solution of 2-(4,4-dimethyl-2-oxo-1,4-dihydro-2H-benzo[d][1,3]oxazin-6-yl)-pyrrole-1-carboxylic acid tert-butyl ester (2.0 g, 5.8 mmol) in THF (anhydrous, 50 mL) at −78° C. was added chlorosulfonyl isocyanate (0.66 mL, 6.7 mmol). After 90 minutes, DMF (9 mL, 116 mmol) was added and the reaction was allowed to warm to room temperature. The reaction mixture was poured into water (50 mL) and extracted with ethyl acetate (2×50 mL). The organic layers were combined, washed with brine (50 mL), dried over magnesium sulfate, filtered and concentrated in vacuo. Purification via flash column chromatography on silica gel (30% ethyl acetate/hexane) gave 2-(4,4-dimethyl-2-oxo-1,4-dihydro-2H-benzo[d][1,3]oxazin-6-yl)-5-cyano-pyrrole-1-carboxylic acid tert-butyl ester (1.1 g, 52%) as a white powder, mp 165-167° C. $^1$H NMR ($d_6$-DMSO, 300 MHz) δ 1.36 (s, 9H), 1.61 (s, 6H), 6.44 (d, 1H, J=3.7 Hz), 6.92 (d, 1H, J=8.2 Hz), 7.27-7.32 (m, 2H), 7.36 ('d', 1H, J=1.5 Hz), 10.36 (s, 1H). MS (EI) m/z 367 [M]$^+$.

2-(4,4-Dimethyl-2-oxo-1,4-dihydro-2H-benzo[d][1,3]oxazin-6-yl)-5-cyano-pyrrole-1-carboxylic acid tert-butyl ester (1 g, 2.7 mmol) was placed in a 25 mL round bottomed flask stoppered with a rubber septum and equipped with a nitrogen inlet and a needle to allow gaseous outflow. A vigorous flow of nitrogen was maintained as the flask was placed in an oil bath and heated to 160° C. After 20 minutes at this temperature, the flask was removed from the oil bath and allowed to cool. The yellow residue was washed into a larger flask with dichloromethane/ethyl acetate and adsorbed onto a small amount of silica gel. Purification by flash column chromatography on silica gel (40% ethyl acetate/hexane) gave the title compound (340 mg, 47%) as a yellow powder, mp 241-242° C. $^1$H NMR ($d_6$-DMSO, 300 MHz) δ 1.65 (s, 6H), 6.67 (d, 1H, J=3.9 Hz), 6.91 (d, 1H, J=8.3 Hz), 6.98 (d, 1H, J=3.9 Hz), 7.61 (dd, 1H, J=1.8, 8.3 Hz), 7.65 ('d', 1H, J=1.6 Hz), 10.32 (s, 1H), 12.54 (bs, 1H). MS (EI) m/z 267 M$^+$. Anal. Calcd. For $C_{15}H_{13}N_3O_2$: C, 67.41; H, 4.90; N, 15.72. Found: C, 67.19; H, 4.96; N, 15.35.

EXAMPLE 2

5-(2'-Oxo-2',3'-dihydrospiro[cyclohexane-1,3'-[3H]indol]-5'-yl-2-cyanopyrrole

A solution of oxindole (25 g, 0.19 mol) in anhydrous tetrahydrofuran (800 mL) was cooled to −20° C., then n-butyllithium (2.5M in hexanes, 152 mL, 0.38 mol) was added slowly followed by N,N,N',N'-tetramethylethylenediamine (51 mL, 0.38 mol). After 15 min. 1,5-diiodopentane (174 g, 0.54 mol) was added slowly and the mixture was allowed to warm to room temperature. After stirring for 16 hours saturated aqueous ammonium chloride solution (1L) and EtOAc (1L) were added. After 15 minutes, the layers were separated and the aqueous phase was extracted using EtOAc (×2). The combined organic layers were extracted with hydrochloric acid (1N), then washed with brine (500 mL), dried (MgSO$_4$), and concentrated to obtain an oil. The oil was triturated with hexane (200 mL) and benzene (20 mL). The precipitate was collected and dried in vacuo to obtain spiro[cyclohexane-1,3'-[3H]indol]-2'-(1'H)one (26.3 g, 69.6%) as colorless crystals: mp 110-114° C.; $^1$H NMR (DMSO-$d_6$) δ 1.67 (m, 10H), 6.84 (d, 1H, J=8 Hz) 6.94 (t, 1H, J=8 Hz), 7.17 (t, 1H, J=8 Hz), 7.44 (d, 1H, J=8 Hz), 10.3 (s, 1H).

To a solution of spiro[cyclohexane-1,3'-[3H]indol]-2'(1'H)-one (17.6 g, 9 mmol) in acetic acid (300 mL) was added sodium acetate (8.0 g, 0.1 mol) and bromine (14.6 g, 91 mmol) with stirring. After 30 minutes at room temperature, the reaction mixture was partitioned between water and EtOAc. The aqueous phase was extracted twice with EtOAc. The combined organic layers were washed with water, dried (MgSO$_4$) and evaporated and the residue was triturated with hexane. The precipitate was collected, and dried in vacuo to obtain 5'-bromospiro[cyclohexane-1,3'-[3H]indol]-2'(1'H)-one (16.5 g, 67%) as off-white crystals: mp 196-199° C.; $^1$H NMR (DMSO-$d_6$) δ 1.62 (m, 10H), 6.8 (d, 1H, J=6.8 Hz), 7.36 (d, 1H, J=8.2, 1.8 Hz), 7.58 (dd, 1H, J=8.2, 1.8 Hz), 10.44 (s, 1H).

To a solution of 5'-bromo-spiro[cyclohexane-1,3'-indolin]-2'-one (3.4 g, 12 mmol) in 1,2-DME (100 mL) under a nitrogen atmosphere, was added tetrakis(triphenylphosphine)palladium(0) (70 mg, 5 mol %). After 15 minutes, 2-borono-1H-pyrrole-1-carboxylic acid, 1-tert butyl ester (1.3 eq, 3.31 g, 15.6 mmol) and a solution of K$_2$CO$_3$ (2.3 eq, 3.83 g, 27.6 mmol) in water (5 mL) were added sequentially. The solution was heated to 80° C. for 3 hours and allowed to cool. The reaction mixture was poured into water (200 mL) and extracted with EtOAc (2×100 mL). The organic layers were combined, washed with brine (150 mL) and dried over MgSO$_4$. The solution was filtered, concentrated in vacuo, and the residue was purified by flash column chromatography on silica gel (eluting with 30% EtOAc/hexane) to give 2-(1',2'-dihydro-2'-oxospiro[cyclohexane-1,3'-[3H]indol]-5'-yl)-1H-pyrrole-1-carboxylic acid, tert-butyl ester (3.4 g, 76%) as a white powder, mp 177° C. $^1$H NMR (CDCl$_3$; 300 MHz) δ 1.38 (s, 9H), 1.59-1.93 (m, 10H), 6.18 (m, 1H), 6.23 ('t', 1H, J=3 Hz), 6.91 (d, 1H, J=8 Hz), 7.21 (d, 1H, J=8 Hz), 7.34 (m, 1H), 7.44 (s, 1H), 8.33 (br s, 1H, D$_2$Oex). MS ((+)-APCI) m/z 367 [(M+H)$^+$]. Anal. Calcd for $C_{22}H_{26}N_2O_3$: C, 72.11; H, 7.15; N, 7.64. Found: C, 71.7; H, 7.16; N, 7.5.

To a solution of 2-(1',2'-dihydro-2'-oxospiro[cyclohexane-1,3'-[3H]indol]-5'-yl)-1H-pyrrole-1-carboxylic acid, tert-butyl ester (0.75 g, 2 mmol) in THF (anhydrous, 20 mL) at −78° C. was added chlorosulfonyl isocyanate (1.15 eq, 0.23 mL, 2.3 mmol). After 90 min, DMF (20 eq, 3.6 mL, 46 mmol) was added and the reaction was allowed to warm to room temperature. The reaction mixture was poured into water (50 mL) and extracted with ethyl acetate (2×50 mL). The organic layers were combined, washed with brine (50 mL), dried over magnesium sulfate, filtered and concentrated in vacuo. Purification via flash column chromatography on silica gel (30% ethyl acetate/hexane) gave 5-(2'-oxo-2',3'-dihydrospiro[cyclohexane-1,3'-[3H]indol]-5'-yl-2-cyanopyrrole-1-carboxylic acid, tert-butyl ester (0.5 g, 63%) as an oil which crystallized from acetone to give white crystals, mp 156° C. $^1$H NMR ($d_6$-DMSO, 400 MHz) δ 1.32 (s, 9H), 1.50 (m, 3H), 1.60-1.70 (m, 5H), 1.75-1.85 (m, 2H), 6.38 (d, 1H, J=3.7 Hz), 6.87 (d, 1H, J=7.9 Hz), 7.18 (dd, 1H, J=1.5, 7.9 Hz), 7.27 (d, 1H, J=3.7 Hz), 7.48 (d, 1H, J=1.8 Hz), 10.42 (bs, 1H). MS (EI) m/z 391 (M$^+$). Anal. Calcd for $C_{23}H_{25}N_3O_3$: C, 70.57; H, 6.44; N, 10.73. Found: C, 69.82; H, 6.46; N, 10.43.

5-(2'-Oxo-2',3'-dihydrospiro[cyclohexane-1,3'-[3H]indol]-5'-yl-2-cyanopyrrole-1-carboxylic acid, tert-butyl ester (0.25 g, 0.8 mmol) was placed in a 5 mL round bottomed flask stoppered with a rubber septum and equipped with nitrogen inlet and a needle to allow gaseous outflow. A vigorous flow of nitrogen was maintained as the flask was placed in an oil bath and heated to 180° C. After 5 minutes at this temperature, the flask was removed from the oil bath and allowed to cool. The black residue was washed into a larger flask with acetone and adsorbed onto a small amount of silica gel. Purification by flash column chromatography on silica gel (eluting with 30% EtOAc/hexane) gave the title compound (95 mg, 51 %) as a yellow oil which crystallized from dichloromethane to give a grey powder, mp 239 ° C. (dec). $^1$H NMR (DMSO-$d_6$; 300 MHz) δ 1.40-1.90 (m, 10H), 6.60 (m, 1H), 6.88 (d, 1H, J=8.1 Hz), 6.95 (m, 1H), 7.56 (dd, 1H, J=1.8, 8.1 Hz), 7.78 (d, 1H, J=1.3 Hz), 10.42 (s, 1H), 12.50 (s, 1H). MS (EI) m/z 291 (M$^+$). Anal. Calcd for $C_{18}H_{17}N_3O_1$: C, 74.20; H, 5.88; N, 14.42. Found: C, 66.63; H, 5.52; N, 12.46.

EXAMPLE 3

2-(3,3-Dimethyl-2-oxo-2,3-dihydro-1H-indol-5-yl)-2-cyanopyrrole

To a solution 2-(3,3-dimethyl-2-oxo-2,3-dihydro-1H-indol-5-yl)-pyrrole-1-carboxylic acid tert-butyl ester (0.39 g, 1.2 mmol) in THF (anhydrous, 9 mL) at −78° C. was added chlorosulfonyl isocyanate (1.15 eq, 0.12 mL, 1.4 mmol). After 120 min, DMF (20 eq, 1.8 mL, 23 mmol) was added and the reaction was allowed to warm to room temperature. The reaction mixture was poured into water (25 mL) and extracted with ethyl acetate (2×50 mL). The organic layers were combined, washed with brine (50 mL), dried over magnesium sulfate, filtered and concentrated in vacuo. Purification via flash column chromatography on silica gel (1:3 ethyl acetate/hexane) gave 2-(3,3-dimethyl-2-oxo-2,3-dihydro-1H-indol-5-yl)-2-cyanopyrrole-1-carboxylic acid tert-butyl ester (0.21 g, 50%) as a white solid: mp 158.6. $^1$H NMR (DMSO-$d_6$; 300 MHz) δ 1.27 (s, 6H), 1.33 (s, 9H), 6.40 (d, 1H, J=3.8 Hz), 6.90 (d, 1H, J=8.0 Hz), 7.19 (dd, 1H, J=1.8, 8.0 Hz), 7.30 (d, 1H, J=1.5 Hz), 10.50 (s, 1H). MS m/z 350 (M−H)$^-$. Calcd for $C_{19}H_{22}N_2O_3$: C, 68.36; H, 6.02; N, 11.96. Found: C, 66.79; H, 6.03; N, 11.02.

2-(3,3-Dimethyl-2-oxo-2,3-dihydro-1H-indol-5-yl)-pyrrole-1-carboxylic acid tert-butyl ester (0.18 g, 0.51 mmol) was placed in a 50 mL round bottomed flask stoppered with a rubber septum and equipped with a nitrogen inlet and a needle to allow gaseous outflow. A vigorous flow of nitrogen was maintained as the flask was placed in an oil bath and heated to 160° C. After 10 minutes at this temperature, the flask was removed from the oil bath and allowed to cool. The black residue was washed into a larger flask with acetone and adsorbed onto a small amount of flurosil. Purification by flash column chromatography on silica gel (eluting with 1:3 acetone: hexane) gave the title compound (118 mg, 92%) as a white solid mp 255.9-257.9° C. $^1$H NMR (DMSO-$d_6$; 300 MHz) δ 1.29 (s, 6H), 6.60 (m, 1H), 6.89 (d, 1H, J=8.0 Hz), 6.96 (m, 1H), 7.55 (dd, 1H, J=1.4, 8.1 Hz), 7.69 (bs, 1H), 10.47 (s, 1H), 12.48 (s, 1H). MS m/z 250 (M−H)$^-$. Calcd for $C_{20}H_{21}N_3O_3$: C, 71.7; H, 5.21; N, 16.72. Found: C, 71.16; H, 5.58; N, 16.09.

EXAMPLE 4

5-(2'-Oxo-2',3'-dihydrospiro[cyclopentane-1,3'-[3H]indol]-5'-yl)-2-cyanopyrrole

A solution of 5'-bromospiro[cyclopentane-1,3'-[3H]indol]-2'(1H)-one (2.0 g, 7.5 mmol) and tetrakis(triphenylphosphine)palladium(0) (430 mg, 0.3 mmol) in ethylene glycol dimethyl ether (50 mL) was stirred under a flow of nitrogen for 15 minutes. To the solution was added sequentially 1-t-butoxycarbonylpyrrole-2-boronic acid (2.1 g, 9.7 mmol) and potassium carbonate (2.4 g, 17 mmol) in water (10 mL). The mixture was heated to 80° C. for 3 hours and allowed to cool. The reaction mixture was poured into water (50 mL) and extracted with ethyl acetate (3×50 mL). The organic layers were combined, washed with brine (30 mL) and dried over magnesium sulfate. The solution was filtered and concentrated in vacuo. Crystallization from 20% ethyl acetate/hexane gave 2-(1',2'-dihydro-2'-oxospiro [cyclopentane-1,3'-[3H]indol]-5'-yl)-1H-pyrrole-1-carboxylic acid, tert-butyl ester (2.2 g, 83%) as a white powder, mp 179-180.5° C. $^1$H NMR (DMSO-$d_6$, 400 MHz) δ 1.30 (s, 9H), 1.75-1.98 (m, 8H), 6.16 (dd, 1H, J=1.8, 3.3 Hz), 6.22 ('t', 1H, J=3.3, 3.3 Hz), 6.79 (d, 1H, J=7.9 Hz), 7.08 (dd, 1H, J=1.8, 7.9 Hz), 7.14 ('d', 1H, J=1.5 Hz), 7.28 (dd, J=1.9, 3.3 Hz), 10.30 (s, 1H). MS (EI) m/z 352 [M$^+$]. Anal. Calcd for $C_{21}H_{24}N_2O_3$: C, 71.57; H, 6.86; N, 7.95. Found: C, 71.08; H, 6.83; N, 7.74.

To a solution of 2-(1',2'-dihydro-2'-oxospiro[cyclohexane-1,3'-[3H]indol]-5'-yl)-1H-pyrrole-1-carboxylic acid, tert-butyl ester (2.2 g, 6.0 mmol) in THF (anhydrous, 25 mL) was added at −78° C. chlorosulfonyl isocyanate (0.63 mL, 7.0 mmol). After 90 minutes, dimethylformamide (11 mL, 140 mmol) was added and the reaction was allowed to warm to room temperature. The reaction mixture was poured into water (50 mL) and extracted with ethyl acetate (2×50 mL). The organic layers were combined, washed with brine (50 mL), dried over magnesium sulfate, filtered and concentrated in vacuo. Purification via flash column chromatography on silica gel (30% ethyl acetate/hexane) gave 5-(2'-oxo-2',3'-dihydrospiro[cyclopentane-1,3'-[3H]indol]-5'-yl-2-cyanopyrrole-1-carboxylic acid, tert-butyl ester (1.7 g, 75%) as white crystals, mp 167-169° C. $^1$H NMR (DMSO-$d_6$, 400 MHz) δ 1.34 (s, 9H), 1.75-1.98 (m, 8H), 6.39 (d, 1H, J=3.7 Hz), 6.84 (d, 1H, J=7.9 Hz), 7.17 (dd, 1H, J=1.8, 7.9 Hz), 7.28 ('t', 2H), 10.41 (s, 1H). MS (ESI) mn/z 376 [M−H]$^-$. Anal. Calcd. for $C_{22}H_{23}N_3O_3$: C, 70.01; H, 6.14; N, 11.13. Found: C, 69.67; H, 6.38; N, 11.04.

5-(2'-Oxo-2',3'-dihydrospiro[cyclopentane-1,3'-[3H]indol]-5'-yl-2-cyanopyrrole-1-carboxylic acid, tert-butyl ester (1 g, 2.7 mmol) was placed in a 25 mL round bottomed flask stoppered with a rubber septum and equipped with nitrogen inlet and a needle to allow gaseous outflow. A vigorous flow of nitrogen was maintained as the flask was placed in an oil bath and heated to 165° C. After 20 minutes at this temperature, the flask was removed from the oil bath and allowed to cool. Crystallization from ethyl ether gave the title compound (600 mg, 79%) as a yellow powder, mp 285-286° C. $^1$H NMR (DMSO-$d_6$, 400 MHz) δ 1.75-2.03 (m, 8H), 6.60 (dd, 1H, J=2.4, 3.7 Hz), 6.84 (d, 1H, J=8.1 Hz), 6.94 (dd, 1H, J=2.4, 3.7 Hz), 7.52 (dd, 1H, J=1.8, 8.1 Hz), 7.60 (d, 1H, J=1.8 Hz), 10.38 (s, 1H), 12.45 (s, 1H). MS (ESI) m/z 276 [M−H]$^-$. Anal. Calcd. For $C_{17}H_{15}N_3O$: C, 73.63; H, 5.45; N, 15.15. Found: C, 73.24; H, 5.34; N, 14.96.

EXAMPLE 5

5-(4,4-Dimethyl-2-oxo-1,4-dihydro-2H-3,1-benzoxazin-6-yl)-1-methyl-1H-pyrrole-2 carbonitrile To a solution of 5-(4,4-dimethyl-2-oxo-1,4-dihydro-2H-3,1-benzoxazin-6-yl)-1H-pyrrole-2-carbonitrile (1 eq, 71 mg, 0.27 mmol) in dimethylformamide (0.5 mL) was added potassium carbonate (5 eq, 0.18 g, 0.1.35 mmol). After 10 minutes, iodomethane (3 eq, 0.05 mL, 0.81 mmol) was added and the suspension was stirred for 2h, poured into water (5 mL) and extracted with ethyl acetate (3×5 mL). The layers were separated, the aqueous layer was extracted with ethyl acetate (3×10 mL) and the combined organic layer was washed with brine, dried over MgSO$_4$ and purified by flash column chromatography on silica gel eluting with 30% ethyl acetate/hexane to give 5-(4,4-dimethyl-2-oxo-1,4-dihydro- 2H-3,1-benzoxazin-6-yl)-1-methyl-1H-pyrrole-2-carbonitrile (30 mg, 41%) as a white solid. $^1$H NMR (300 MHz, d$_6$-DMSO) δ 1.64 (s, 6H), 3.71 (s, 3H), 6.33 (d, 1H, J=4.1 Hz), 6.98 (d, 1H, J=8.0 Hz), 7.03 (d, 1H, J=4.1 Hz), 7.39 (m, 2H), 10.39 (s, 1H). MS (APCI (−)) m/z 280 (M−H)$^-$. Anal. calcd for C$_{16}$H$_{15}$N$_3$O$_2$, C, 68.3, H, 5.37, N, 14.9. Found, C, 68.4, H, 5.51, N, 14.6.

EXAMPLE 6

General Method A 5-(4,4-Dimethyl-2-oxo-1,4-dihydro-2H-3,1-benzoxazin-6-yl)-1-ethyl-1H-pyrrole-2-carbonitrile To a solution of 5-(4,4-dimethyl-2-oxo-1,4-dihydro-2H-3,1-benzoxazin-6-yl)-1H-pyrrole-2-carbonitrile (1.3 g, 5 mmol) in dimethylformamide (25 ml) was added potassium carbonate (1 g, 7.5 mmol), and iodoethane (0.4 ml, 5.1 mmol), and the mixture was stirred at room temperature for 3 hours. Ethylacetate and water were added, the ethylacetate layer was separated, dried over magnesium sulfate, and concentrated in vacuo. The residue was recrystallized from ethylacetate/hexane to afford the title compound, m.p. 200-202° C. (0.4 g, 27%); $^1$H-NMR (DMSO-d$_6$) δ 1.25 (t, J=7.2 Hz, 3H), 1.64 (s, 6H), 4.07 (q, J=7.2 Hz, 2H), 6.29 (d, J=4.1 Hz, 1H), 7.0 (d, J=8 Hz, 1H), 7.05 (d, J=4.1 Hz, 1H), 7.34 (m, 2H), 10.42 (s, 1H). MS (ESI (−)) m/z 294 (M−H)$^-$

EXAMPLE 7

5-(4,4-dimethyl-2-oxo-1,4-Dihydro-2H-3,1-benzoxazin-6-yl)-1-prop-2-ynyl-1H-pyrrole-2-carbonitrile 5-(4,4-Dimethyl-2-oxo-1,4,dihydro-2H-3,1-benzoxazin-6-yl)-1H-pyrrol-2-carbonitrile (0.74 g, 2.8 mmol) and propargylbromide (0.5 g, 4.2 mmol) were reacted, according to General Method A, to afford the title compound, m.p. 222-224° C. (0.13 g, 15%). $^1$H-NMR (DMSO-d$_6$) δ 1.65 (s, 6H), 3.64 (t, J=2.3 Hz, 1H), 4.85 (d, J=2.3 Hz, 2H), 6.37 (d, J=4 Hz, 1H), 7.01 (d, J=8.2 Hz, 1H), 7.11 (d, J=4 Hz, 1H), 7.43 (m, 2H), 10.45 (s, 1H), MS (APCI (−)) m/z 304 (M−H)$^-$

EXAMPLE 8 tert-butyl[2-cyano-5-(4,4-dimethyl-2-oxo-1,4-dihydro-2H-3,1-benzoxazin-6-yl)-1H-pyrrol-1-yl]acetate 5-(4,4-Dimethyl-2-oxo-1,4-dihydro-2H-3,1-benzoxazin-6-yl)-1H-pyrrol-2-carbonitrile (5.4 g, 20 mmol) and tert-butylbromoacetate (4.64 g, 22 mmol) were reacted, according to General Method A, to afford the title compound, m.p. 188-190° C. (3 g, 40%). $^1$H-NMR (DMSO-d$_6$) δ 1.35 (s, 9H), 1.62 (s, 6H), 4.8 (s, 2H), 6.35 (d, J=4.3 Hz, 1H), 6.98 (d, J=8.1 Hz, 1H), 7.09 (d, J=4.3 Hz, 1H), 7.26 (m, 2H), 10.42 (s, 1H), MS (APCI (−)) m/z 380 (M−H)$^-$

EXAMPLE 9

[2-Cyano-5-(4,4-dimethyl-2-oxo-1,4-dihydro-2H-3,1-benzoxazin-6-yl)-1H-pyrrol-1yl]acetic acid A solution of tert-butyl[2-cyano-5-(4,4-dimethyl-2-oxo-1,4-dihydro-2H-3,1-benzoxazin-6-yl)-1H-pyrrol-1-yl]acetate (2.2 g, 5.8 mmol), and sodium hydroxide (1.6 g, 40 mmol) in ethanol (200 ml) was heated to reflux for 2 hours. After cooling to room temperature the mixture was acidified with diluted hydrochloric acid, and extracted with ethylacetate. The ethylacetate solution was dried over magnesium sulfate, filtered, and concentrated in vacuo. Recrystallization from ethylacetate/hexane afforded the title compound, m.p. 207-209° C. (1.2 g, 64%); $^1$H-NMR (DMSO-d$_6$) δ 1.61 (s, 6H), 4.77 (s, 2H), 6.35 (d, J=4 Hz, 1H), 6.98 (d, J=8.1 Hz, 1H), 7.09 (d, J=4.1 Hz, 1H), 7.26 (m, 2H), 10.43 (s, 1H), MS (APCI (−)) m/z 324 (M−H)$^-$.

EXAMPLE 10

2-[2-cyano-5-(4,4-dimethyl-2-oxo-1,4-dihydro-2H-3,1-benzoxazin-6-yl)-1H-pyrrol-1-yl]-N-[2-(3-ethoxy-4-methoxyphenyl)ethyl]acetamide A solution of [2-cyano-5-(4,4-dimethyl-2-oxo-1,4-dihydro-2H-3,1-benzoxazin-6-yl)-1H-pyrrol-1-yl]acetic acid (0.6 g, 1.8 mmol), 3-ethoxy-4-methoxyphenylethylamine (0.36 g, 1.9 mmol), diiso-propylethylamine (0.26 g, 2 mmol), and O-(7-azabenzotriazol-1-yl)-N,N,N',N'-tetramethyluronium hexafluorophosphate (0.7 g, 1.8 mmol) in dimethylformamide (20 ml) was stirred at room temperature for 20 hours. The mixture was diluted with water and extracted with ethylacetate. The ethylacetate solution was washed with brine, dried over magnesium sulfate, and concentrated in vacuo. The residue was recrystallized from ethanol to afford the title compound, m.p. 160-162° C. (0.2 g, 22%): $^1$H-NMR (DMSO-d$_6$) δ 1.3 (t, J=6.9 Hz, 3H), 1.59 (s, 6H), 2.61 (t, 2H, J=7 Hz), 3.29 (q, J=6.9 Hz, 2H), 3.71 (s, 3H), 3.97 (q, J=6.9 Hz, 2H), 4.6 (s, 2H), 6.32 (d, J=5.1 Hz, 1H), 6.65 (dd, J=7.6, 2.0 Hz, 1H), 6.77 (d, J=2.3, 1H), 6.83 (d, J=8.3 Hz, 1H), 6.96 (d, J=8.7 Hz, 1H), 7.05 (d, J=4.1 Hz, 1H), 7.26 (m, 2H), 8.3 (t, J=6 Hz, 1H), 10.42 (s, 1H), MS (APCI (+)) m/z 503 (M+H)$^+$

EXAMPLE 11

5-(4,4-Dimethyl-2-oxo-1,4-dihydro-2H-3,1-benzoxazine-6-yl)-1-pentyl-1H-pyrrole-2-carbonitrile 5-(4,4-Dimethyl-oxo-1,4-dihydro-2H-3,1-benzoxazine-6-yl)-1H-pyrrole-carbonitrile (1.94 g, 7.3 mmol) was reacted, according to General Method A, with 1-iodopentane (1.5 g, 7.6 mmol) to afford the title compound, m.p. 128-131° C. (0.2 g, 8%); $^1$H-NMR (DMSO-d$_6$) δ 0.73 (t, J=7.3 Hz, 3H), 1.05 (m, 2H), 1.14 (m, 2H), 1.57 (m, 2H), 1.63 (s, 6H), 4.04 (t, J=7.5 Hz, 2H), 6.28 (d, J=4 Hz, 1H), 6.98 (d, J=7.9 Hz, 1H), 7.04 (d, J=4.5 Hz, 1H), 7.33 (dd, J=8.9, 2.0 Hz, 1H), 7.37 (d, J=2.2 Hz, 1H), 10.41 (s, 1H), MS (APCI (−)) m/z 336 (M−H)$^-$

EXAMPLE 12

5-(1,4,4-trimethyl-2-oxo-1,4-dihydro-2H-3,1-benzoxazin-6-yl)-1H-pyrrole-2-carbonitril tert-Butyl 2-cyano-5-(1,4,4-trimethyl-2-oxo-1,4-dihydro-2H-3,1-benzoxazin-6-yl)-1H-pyrrole-1-carboxylate.

To a solution of 2-(4,4-Dimethyl-2-oxo-1,4-dihydro-2H-benzo[d][1,3]oxazin-6-yl)-5-cyano-pyrrole-1-carboxylic acid tert-butyl ester (0.5 g, 1.4 mmol, 1 eq) in DMF (anhydrous, 25 mL) was added NaH (60% dispersion in oil, 65 mg, 1.6 mmol, 1.2 eq) at 0° C. After 15 min, methyl iodide (0.25 mL, 4.1 mmol, 3 eq) was added and the reaction was allowed to warm to room temperature over night. The reaction mixture was poured into water (50 mL) and extracted with ethyl acetate (2×50 mL). The organic layers were combined, washed with brine (50 mL), dried over magnesium sulfate, filtered and concentrated in vacuo to give the product (0.5 g, 94%) as an off-white solid, mp 143-145° C.: $^1$H NMR (300 MHz, d$_6$-DMSO) δ 1.38 (s, 9H), 1.62 (s, 6H), 3.33 (s, 3H), 6.48 (d, 1H, J=3.8 Hz), 7.13 -7.16 ('dd', 1H), 7.33 (d, 1H, J=3.8 Hz), 7.40-7.43 (m, 2H). MS (ESI (+)) [M+H]$^+$=382. Anal. calcd. for C$_{21}$H$_{23}$N$_3$O$_4$: C, 66.13; H, 6.08; N, 11.02. Found: C, 65.46; H, 6.16, N, 11.02.

tert-Butyl 2-cyano-5-(1,4,4-trimethyl-2-oxo-1,4-dihydro-2H-3,1-benzoxazin-6-yl)-1H-pyrrole-1-carboxylate (180 mg, 0.47 mmol) was placed in a 25 mL round bottomed flask stoppered with a rubber septum and equipped with nitrogen inlet and a needle to allow gaseous outflow. A vigorous flow of nitrogen was maintained as the flask was placed in an oil bath and heated to 150° C. After 20 minutes at this temperature, the flask was removed from the oil bath and allowed to cool. To the solid was added acetone/dichloromethane. The solid was filtered to give the product (100 mg, 76%) as an off-white solid, mp 256-7° C. (dec.): $^1$H NMR (300 MHz, d$_6$-DMSO) δ 1.65 (s, 6H), 3.33 (s, 3H), 6.74 (dd, 1H, J=2.6, 3.6 Hz), 7.00 (dd, 1H, J=2.2, 3.8 Hz), 7.15 (d, 1H, J=8.5 Hz), 7.67 (d, 1H, J=1.9 Hz), 7.73 (dd, 1H, J=1.19, 8.5 Hz), 12.62 (s, 1H). MS (ESI (+)) [M+H]$^+$=282. Anal. calcd. for C$_{16}$H$_{15}$N$_3$O$_2$: C, 68.31; H, 5.37; N, 14.94. Found: C, 67.87; H, 5.42, N, 14.75.

EXAMPLE 13

4-Bromo-5-(4,4-dimethyl-2-oxo-1,4-dihydro-2H-3,1-benzoxazin-6-yl)-1-methyl-1H-pyrrole-2-carbonitrile To a solution of tert-butyl 6-(5-cyano-1-methyl-1H-pyrrol-2-yl)-4,4-dimethyl-2-oxo-2H-3,1-benzoxazine-1(4H)-carboxylate (1 eq, 1.94 g, 5.10 mmol) in THF (150 mL) at −78° C. was added N-bromosuccinimide (1.1 eq, 1.0 g, 5.61 mmol). The solution was allowed to warm and stir for 16 hours. Pyridine (1 mL) was added and the mixture was poured into water (150 mL), the layers were separated, the aqueous layer was extracted with ethyl acetate (3 ×10 mL) and the combined organic layer was washed with brine, dried over MgSO$_4$ and concentrated in vacuo. The product, tert-butyl 6-(3-bromo-5-cyano-1-methyl-1H-pyrrol-2-yl)-4,4-dimethyl-2-oxo-2H-3,1-benzoxazine-1(4H)-carboxylate was obtained by crystallization from 20% ethyl acetate/hexane as a white crystalline solid. $^1$H NMR (300 MHz, d$_6$-DMSO) δ 1.56 (s, 9H), 1.71 (s, 6H), 3.65 (s, 3H), 7.30 (s, 1H), 7.44 (d, 1H, J=8.4 Hz), 7.52 (d, 1H, J=8.4 Hz), 7.55 (s, 1H). M/z (ESI (+)) 461 (M+H)$^+$. Anal. calcd for C$_{21}$H$_{22}$N$_3$O$_4$, C, 54.8, H, 4.82, N, 9.13. Found, C, 54.9, H, 4.86, N, 9.1.

A solution of tert-butyl 6-(3-bromo-5-cyano-1-methyl-1H-pyrrol-2-yl)-4,4-dimethyl-2-oxo-2H-3,1-benzoxazine-1(4H)-carboxylate (1 eq, 0.4 g, 0.87 mmol) in THF was added to a solution of sodium ethoxide (3 eq, 0.18 g, 2.6 mmol) in ethanol (10 mL). The solution was heated at 80° C. for 1 hour, then cooled to room temperature, and concentrated in vacuo. The residue was dissolved in THF (10 mL) and 4N HCl (10 mL) was added. After heating to 60° C. for 16 hours the solution was cooled, poured into water and the layers were separated. The aqueous layer was extracted with ethyl acetate (3×10 mL) and the combined organic layer was washed with brine, dried over MgSO$_4$ and concentrated in vacuo. The product, 4-bromo-5-(4,4-dimethyl-2-oxo-1,4-dihydro-2H-3,1-benzoxazin-6-yl)-1-methyl-1H-pyrrole-2-carbonitrile (0.17 g, 54%) was obtained by crystallization from 20% ethyl acetate/hexane. $^1$H NMR (300 MHz, d$_6$-DMSO) δ 1.64 (s, 6H), 3.62 (s, 3H), 7.02 (d, 1H, J=8.2 Hz), 7.34 (s, 1H), 7.35 (dd, 1H, J=1.3, 8.2 Hz), 7.40 (s, 1H), 10.47 (s, 1H). MS (ESI (−)) m/z 358/360 (M−H)$^−$. Anal. calcd for C$_{16}$H$_{14}$N$_3$O$_2$Br, C, 53.4, H, 3.92, N, 11.7. Found, C, 52.6, H, 3.82, N, 11.2.

EXAMPLE 14

5-(4,4-Dimethyl-2-oxo-1,4-dihydro-2H-3,1-benzoxazin-6-yl)-1,4-dimethyl-1H-pyrrole-2-carbonitrile A solution of 4-bromo-5-(4,4-dimethyl-2-oxo-1,4-dihydro-2H-3,1-benzoxazin-6-yl)-1-methyl-1H-pyrrole-2-carbonitrile (70 mg, 0.2 mmol), PhCNPdCl(PPh$_3$)$_2$ (cat., 7 mg) and tetramethyltin (10 eq, 0.35 g, 2 mmol) in HMPA (3 mL) was heated to 110° C. for 5 days. The solution was allowed to cool, poured into water (20 mL) and extracted with ethyl acetate (3×5 mL). The combined organic layer was washed with brine, dried over MgSO$_4$ and purified by flash column chromatography on silica gel eluting with 30% ethyl acetate/hexane to give 5-(4,4-dimethyl-2-oxo-1,4-dihydro-2H-3,1-benzoxazin-6-yl)-1,4-dimethyl-1H-pyrrole-2-carbonitrile (36 mg, 63%) as a white solid. $^1$H NMR (300 MHz, d$_6$-DMSO) δ 1.64 (s, 6H), 1.97 (s, 3H), 3.56 (s, 3H), 6.87 (s, 1H), 7.00 (d, 2H, J=8.1 Hz), 7.28 (dd, 1H, J=8.1, 1.6 Hz), 7.32 (s, 1H), 10.40 (s, 1H) MS (ESI (−)) 294 (M−H)$^−$. Anal. calcd for C$_{17}$H$_{17}$N$_3$O$_2$, C, 69.1, H, 5.8, N,14.2. Found, C, 69.1, H, 5.72, N, 14.0.

EXAMPLE 15 tert-Butyl 5-cyano-2-(4,4-dimethyl-2-oxo-1,4-dihydro-2H-3,1-benzoxazin-6-yl)-3-nitro-1H-pyrrole-1-carboxylate To a solution of 2-(4,4-Dimethyl-2-oxo-1,4-dihydro-2H-benzo[d][1,3]oxazin-6-yl)-5-cyano-pyrrole-1-carboxylic acid tert-butyl ester (3.0 g, 8.2 mmol, 1 eq) in acetic anhydride (50 mL) was added Cu(NO$_3$)$_2$.2.5 H$_2$O (1.04 g, 4.5 mmol, 0.55 eq). After the reaction mixture stirred at room temperature for 24 hours, it was poured into saturated aqueous sodium bicarbonate solution (100 mL) and extracted with ethyl acetate (2×100 mL). The organic layers were combined, washed with water (50 mL) and brine (50 mL), dried over magnesium sulfate, filtered and concentrated in vacuo. Purification by flash column chromatography (20% ethyl acetate/hexane) on silica gel gave the product as a yellow solid (0.54 g, 16%). $^1$H NMR (500 MHz, d$_6$-DMSO) δ 1.25 (s, 9H), 1.60 (s, 6H), 6.97 (d, 1H, J=8.2 Hz), 7.38 (dd, 1H, J=1.8, 8.2 Hz), 7.49 (d, 1H, J=1.8 Hz), 8.09 (s, 1H), 10.47 (s, 1H). MS (ESI (−)) [M−H]$^−$=411. Anal. calcd. for C$_{20}$H$_{20}$N$_4$O$_6$: C, 58.25; H, 4.89; N, 13.59. Found: C, 58.72; H, 5.14, N, 13.39.

EXAMPLE 16

4-Amino-5-(4,4-dimethyl-2-oxo-1,4-dihydro-2H-3,1-benzoxazin-6-yl)-1H-pyrrole-2-carbonitrile A solution of 4-nitro-5-(4,4-dimethyl-2-oxo-1,4-dihydro-2H-3,1-benzoxazin-6-yl)-1H-pyrrole-2-carbonitrile (0.4 g, 1.28 mmol) in ethanol/water (5:1, 20 mL) was treated sequentially with zinc powder (2.5 wt, 1.0 g) and ammonium chloride (5 wt, 2.0 g). The suspension was heated at 80° C. or 30 min, cooled to room temperature, poured into water (30 mL) and extracted with ethyl acetate (3×15 mL). The combined organic layer was washed with brine, dried over MgSO$_4$ and purified by flash column chromatography on silica gel eluting with ethyl acetate to give 4-amino-5-(4,4-dimethyl-2-oxo-1,4-dihydro-2H-3,1-benzoxazin-6-yl)-1H-pyrrole-2-carbonitrile (0.29 g, 80%) as a yellow solid. $^1$H NMR (500 MHz, d$_6$-DMSO) δ 81.63 (s, 6H), 4.29 (s, 2H), 6.39 (s, 1H), 6.89 (d, 1H, J=8.1 Hz), 7.49 (s, 1H), 7.52 (dd, 1H, J=8.1 and 2.3 Hz), 10.25 (s, 1H), 11.76 (s, 1H). MS (ESI (−)) m/z 281 (M−H)$^−$.

Anal. calcd for $C_{15}H_{14}N_4O_2$, C, 63.8, H, 5.00, N, 19.9. Found, C, 63.7, H, 5.10, N, 19.82

EXAMPLE 17

5-(4,4-dimethyl-2-oxo-1,4-dihydro-2H-3,1-benzoxazin-6-yl)-3-nitro-1H-pyrrole-2-carbonitrile To 4,4-Dimethyl-6-(5-cyano-1H-pyrrol-2-yl)-1,4-dihydrobenzo[d][1,3]oxazin-2-one (0.3 g, 1.2 mmol, 1 eq) in acetic anhydride (7.3 mL) was added $Cu(NO_3)_2.2.5 H_2O$ (0.15 g, 0.65 mmol, 0.55 eq). After the reaction mixture stirred at room temperature for 2 hours, it was poured into saturated aqueous sodium bicarbonate solution (50 mL) and extracted with ethyl acetate (2×50 mL). The organic layers were combined, washed with water (50 mL) and brine (50 mL), dried over magnesium sulfate, filtered and concentrated in vacuo. The residue crystallized from dichloromethane/acetone to give the product as a yellow solid (48 mg, 13%). The filtrate (0.3 g) was placed aside. $^1$H NMR (300 MHz, $d_6$-DMSO) δ 1.65 (s, 6H), 6.94 (d, 1H, J=8.3 Hz), 7.51 (s, 1H), 7.73 (d, 1H, J=8.3 Hz), 7.78 (s, 1H), 10.46 (s, 1H), 13.84 (s, 1H). MS (ESI (−)) [M−H]⁻ m/z 311. Anal. calcd. for $C_{15}H_{12}N_4O_4$: C, 57.69; H, 3.87; N, 17.94. Found: C, 57.91; H, 3.96, N, 17.41.

EXAMPLE 18

3-amino-5-(4,4-dimethyl-2-oxo-1,4-dihydro-2H-3,1-benzoxazin-6-yl)-1H-pyrrole-2-carbonitrile To 5-(4,4-dimethyl-2-oxo-1,4-dihydro-2H-3,1-benzoxazin-6-yl)-3-nitro-1H-pyrrole-2-carbonitrile (0.14 g, 0.45 mmol) in $EtOH/H_2O$ (5:1, 20 mL:4 mL) was added Zn powder (0.35 g, 5.3 mmol) and $NH_4Cl$ (0.70 g, 13 mmol) and the mixture was heated to 60° C. for 25 minutes. After cooling to room temperature and stirring 24 h, the reaction mixture was diluted with ethyl acetate (100 mL) and filtered through a pad of celite. The filtrate was washed with water (50 mL) and brine (50 mL), dried over magnesium sulfate, filtered and concentrated in vacuo. Purification by flash column chromatography (60% ethyl acetate/hexane) on silica gel gave the product as an orange foam (30 mg, 24%). $^1$H NMR (500 MHz, $d_6$-DMSO) δ 1.63 (s, 6H), 5.01 (s, 2H), 5.95 (d, 1H, J=2.9 Hz), 6.87 (d, 1H, J=8.3 Hz), 7.48 (dd, 1H, J=2.0, 8.3 Hz), 7.54 (d, 1H, J=2.0 Hz), 10.30 (s, 1H), 11.17 (d, 1H, J=2.5 Hz). MS (ESI) [M−H]⁻ m/z 281.

EXAMPLE 19

5-(4,4-Dimethyl-2-oxo-1,4-dihydro-2H-3,1-benzoxazin-6-yl)-1,3,4-trimethyl-1H-pyrrol-2-carbonitrile To a solution of 5-(4,4-dimethyl-2-oxo-1,4-dihydro-2H-3,1-benzoxazin-6-yl)-1,4-dimethyl-1H-pyrrole-2-carbonitrile (1 eq, 0.15 g, 0.51 mmol) in THF (5 mL) at −78° C. was added N-bromosuccinimide (1.1 eq, 0.1 g, 0.56 mmol). The solution was allowed to warm and stir for 16 hours. Pyridine (1 mL) was added and the mixture was poured into water (15 mL), the layers were separated, the aqueous layer was extracted with ethyl acetate (3×10 mL) and the combined organic layer was washed with brine, dried over $MgSO_4$ and concentrated in vacuo. The product, 5-(4,4-dimethyl-2-oxo-1,4-dihydro-2H-3,1-benzoxazin-6-yl)-3-bromo-1,4-dimethyl-1H-pyrrole-2-carbonitrile was obtained by crystallization from 20% ethyl acetate/hexane as a white crystalline solid. $^1$H NMR (300 MHz, $d_6$-DMSO) δ 1.64 (s, 6H), 1.93 (s, 3H), 3.57 (s, 3H), 7.01 (d, 1H, J=8 Hz), 7.31 (dd, 1H, J=1.95, 8 Hz), 7.35 (s, 1H), 10.43 (s, 1H). MS m/z (ESI (−)) 372/374 (M−H)⁻. Anal. calcd for $C_{17}H_{16}N_3O_2$, C, 54.6, H, 4.31, N, 11.2. Found, C, 54.8, H, 4.42, N, 11.1.

A solution of 5-(4,4-dimethyl-2-oxo-1,4-dihydro-2H-3,1-benzoxazin-6-yl)-3-bromo-1,4-dimethyl-1H-pyrrole-2-carbonitrile (0.11 g, 0.29 mmol), $PhCNPdCl(PPh_3)_2$ (cat., 11 mg) and tetramethyltin (10 eq, 0.53 g, 2.9 mmol) in HMPA (3 mL) was heated to 110° C. for 5 days. The solution was allowed to cool, poured into water (20 mL) and extracted with ethyl acetate (3×15 mL). The combined organic layer was washed with brine, dried over $MgSO_4$ and purified by flash column chromatography on silica gel eluting with 30% ethyl acetate/hexane to give 5-(4,4-dimethyl-2-oxo-1,4-dihydro-2H-3,1-benzoxazin-6-yl)-1,3,4-trimethyl-1H-pyrrole-2-carbonitrile (77 mg, 85%) as a white solid. $^1$H NMR (300 MHz, $d_6$-DMSO) δ 1.63 (s, 6H), 1.87 (s, 3H), 2.49 (s, 3H), 3.50 (s, 3H), 6.99 (d, 1H, J=8.2 Hz), 7.25 (dd, 1H, J=8.2, 1.4 Hz), 7.29 (s, 1H), 10.39 (s, 1H). MS (ESI (−)) 308 (M−H)⁻. Anal. calcd for $C_{18}H_{19}N_3O_4$, C, 69.9, H, 6.19, N, 13.6. Found, C, 68.8, H, 6.22, N, 12.9

EXAMPLE 20

4-bromo-(4,4-dimethyl-2-oxo-1,4-dihydro-2H-3,1-benzoxazin-6-yl)-1H-pyrrole-2-carbonitrile To 4,4-Dimethyl-6-(5-cyano-1H-pyrrol-2-yl)-1,4-dihydrobenzo[d][1,3]oxazin-2-one (0.625 g, 2.3 mmol, 1 eq) in THF (anhydrous, 60 mL) was added NBS (0.46 g, 2.5 mmol, 1.1 eq) at −78° C. After 1 hour, the reaction was warmed to room temperature, poured into water (100 mL) and extracted with ethyl acetate (2×100 mL). The organic layers were combined, washed with aqueous 10% sodium bisulfite solution (50 mL), water (50 mL) and brine (50 mL), dried over magnesium sulfate, filtered and concentrated in vacuo. Crystallization from 20% ethyl acetate/hexane gave the product (40 mg, 5%) as a white solid. The filtrate (0.5 g) was placed aside. $^1$H NMR (300 MHz, $d_6$-DMSO) δ 1.64 (s, 6H), 6.98 (d, 1H, J=8.2 Hz), 7.19 (d, 1H, J=1.4 Hz), 7.57 (s, 1H), 7.62 (dd, 1H, J=1.4, 8.3 Hz), 10.43 (s, 1H), 12.91 (s, 1H). MS (ESI) [M−H]⁻ m/z 344/346. Anal. calcd. for $C_{15}H_{12}BrN_3O_2$: C, 52.04; H, 3.49; N, 12.14. Found: C, 51.4; H, 3.57, N, 11.59.

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

What is claimed is:

1. A method of providing progestational therapy to a mammal having endometriosis or fibroids, wherein said method comprises administering a progestationally effective amount of a compound having the structure of formula 1:

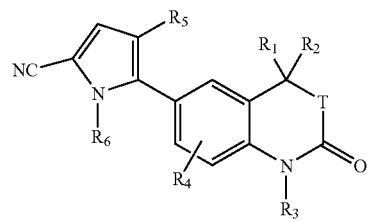

wherein:

T is S;

$R_1$ and $R_2$ are each, independently, hydrogen or $C_1$ to $C_6$ alkyl; or $R_1$ and $R_2$ are taken together to form —$CH_2(CH_2)_nCH_2$;

n=1-5;

$R_3$ is hydrogen, $R_4$ is hydrogen, $R_5$ hydrogen, $R_6$ is hydrogen or $C_1$ to $C_6$ alkyl;

$R_7$ is hydrogen or alkyl;

or a pharmaceutically acceptable salt thereof, to said mammal.

2. The method according to claim 1, wherein in formula 1: $R_1$ and $R_2$ are each, independently, hydrogen or $CH_1$ to $CH_6$ alkyl.

3. The method according to claim 1, wherein said progestationally effective amount is 0.02 μg/kg to 750 μg/kg.

4. The method according to claim 1, wherein said $R_1$ and $R_2$ are taken together to form —$CH_2(CH_2)_nCH_2$— and n is 1.

5. The method according to claim 1, wherein said $R_1$ and $R_2$ are taken together to form —$CH_2(CH_2)_nCH_2$— and n is 2.

6. The method according to claim 1, wherein $R_1$ and $R_2$ are $CH_1$ to $CH_6$ alkyl.

* * * * *